United States Patent [19]

Muchowski et al.

[11] Patent Number: 4,935,440

[45] Date of Patent: Jun. 19, 1990

[54] 3-[ω-(3,5-DI-T-BUTYL-4-HYDROXYPHENYL-)ALKYL]PYRROLES, AND ANTI-INFLAMMATORY USES THEREOF

[75] Inventors: Joseph M. Muchowski, Sunnyvale; Robert Greenhouse, Newark; John Young, Redwood City; D. V. Krishna Murthy, Cupertino, all of Calif.

[73] Assignee: Syntex (U.S.A.) Inc., Palo Alto, Calif.

[21] Appl. No.: 313,658

[22] Filed: Feb. 21, 1989

Related U.S. Application Data

[62] Division of Ser. No. 936,551, Nov. 25, 1986, Pat. No. 4,833,166.

[51] Int. Cl.$^5$ .................. A61K 31/10; C07D 207/36; C07D 207/32
[52] U.S. Cl. .................... 514/423; 548/543; 548/544
[58] Field of Search .............. 548/544, 543, 560, 561, 548/562; 514/423

[56] References Cited

U.S. PATENT DOCUMENTS

| | | | |
|---|---|---|---|
| 3,285,931 | 11/1966 | Huisgen | 260/313.1 |
| 3,551,571 | 12/1970 | Pachter et al. | 424/274 |
| 3,644,631 | 2/1972 | Pachter et al. | 424/272 |
| 3,876,660 | 4/1975 | Bailey | 260/326.5 |
| 3,963,480 | 6/1976 | Bailey | 71/95 |
| 4,000,160 | 12/1976 | Bailey | 260/326.5 |
| 4,066,614 | 1/1978 | Oppelt et al. | 260/45.8 |
| 4,124,725 | 11/1978 | Moore | 424/330 |
| 4,128,664 | 12/1978 | Moore | 424/324 |
| 4,140,696 | 2/1979 | Tarzia et al. | 260/326.5 |
| 4,172,082 | 10/1979 | Moore | 549/72 |
| 4,172,151 | 10/1979 | Moore | 424/330 |
| 4,418,074 | 11/1983 | Moore | 424/274 |

OTHER PUBLICATIONS

Moore et al., "2,6-Di-tert-butyl-4-(2'-theonyl)phenol (R-830): A Novel Nonsteroidal Anti-Inflammatory Agent with Antioxidant Properties", Agents and Actions, 12(5): 674–683 (1982).

Hidaka et al., "Inhibition of Cyclooxygenase and 5-lipoxygenase by a New Antiinflammatory Drug, α-(3-,5-Di-t-butyl-4-hydroxybenzylidene)-γ-butyrolactone", Chem. Abs., 103: 15391p, Ensho, 3(4): 511–512 (1983).

Isomura et al., "Studies on the Synthesis and Anti-Inflammatory Activity of 2,6-Di-tert-butylphenols with a Heterocyclic Group at the 4-Position. I", Chem. Pharm. Bull., 31(9): 3168–3178 (1983).

Isomura et al., "Studies on the Synthesis and Anti-Inflammatory Activity of 2,6-Di-tert-butylphenols with a Heterocyclic Group at the 4-Position, II", Chem. Pharm. Bull., 31(9): 3179–3185 (1983).

Isomura et al., "Studies on the Synthesis and Anti-Inflammatory Activity of 2,6-Di-tert-butylphenols with a Heterocyclic Group at the 4-Position. III", Chem. Pharm. Bull., 32(1): 152–165 (1984).

Isomura et al., "Studies on the Synthesis and Anti-Inflammatory Activity of 2,6-Di-tert-butylphenols with a Heterocyclic Group at the 4-Position. V. Elimination Reaction of the Sylfinyl Group of 2,3-dihydroimidazo[2,1-b]- thiazole 1-Oxide", Chem. Pharm. Bull., 32(12): 4726–4730 (1984).

Moore et al., "SAR of Antioxidant-Antiinflammatory Agents: Di-t-Butyl Phenols and Other Series", 19th National Medicinal Chemical Symposium of the ACS, Tuscon, Ariz., 151–154, Jun. 17–21, 1984.

*Primary Examiner*—David B. Springer
*Attorney, Agent, or Firm*—David A. Lowin; Tom M. Moran

[57] ABSTRACT

3-[ω-(3,5-Di-t-butyl-4-hydroxyphenyl)alkanoyl]-pyrroles and their de-oxy analogs, for example, 3-(3,5-di-t-butyl-4-hydroxybenzyl)pyrrole, 2-chloro-4-(3,5-di-t-butyl-4-hydroxybenzoyl)pyrrole, 3-(3,5-di-t-butyl-4-hydroxybenzoyl)pyrrole and 3-[2-(3,5-di-t-butyl-4-hydroxyphenyl)-1-oxoethyl]pyrrole, have high pharmacological potency as anti-inflammatory, analgesic and antipyretic agents.

21 Claims, No Drawings

3-[ω-(3,5-DI-T-BUTYL-4-HYDROXYPHENYL)AL-KYL]PYRROLES, AND ANTI-INFLAMMATORY USES THEREOF

This is a division of pending application Ser. No. 936,551, filed Nov. 25, 1986, U.S. Pat. No. 4,833,166, incorporated herein by reference.

BACKGROUND OF THE INVENTION

1. Field of the Invention

The present invention relates to compounds having pharmacological activity, more specifically to nonsteroidal anti-inflammatory agents, analgesics and antipyretics, and particularly to a series of 3-[ω-(3,5-di-t-butyl-4-hydroxyphenyl)alkanoyl]pyrroles and their deoxy analogs.

2. Background Information and Related Art

The use of certain pyrroloyl compounds as nonsteroidal anti-inflammatory agents is known. For example, U.S. Pat. No. 4,418,074 (to Moore) describes:

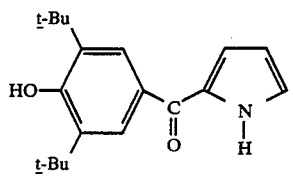

2,6-di(t-butyl)-4-(2'-pyrroloyl)phenol and reference is made to several other U.S. patents in which substitutions at the 4-position of 2,6-di(t-butyl)-phenols are taught, including: an N-substituted carboxamido group (4,128,664), an optionally substituted benzoyl group (4,124,725), an optionally substituted phenyl group (4,172,151), and optionally substituted thiophenyl groups (4,172,082).

Other compounds having the di-t-butyl-hydroxyphenyl moiety have been proposed as anti-inflammatory agents, including:

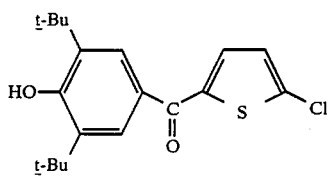

2,6-di-t-butyl-4-(2'-thenoyl)phenol

[Moore and Swingle, *Agents and Actions*, 12(5): 674–683 (1982)];

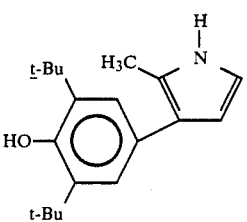

2,6-di-t-butyl-4-(5'-chloro-2'-thenoyl)phenol

[Moore, Bell and Swingle, "SAR of Antioxidant-Antiinflammatory Agents: Di-t-Butyl Phenols and Other Series", 19th *National Medicinal Chemical Symposium of the ACS*, Tucson, AZ, 151–154, June 17–21, 1984];

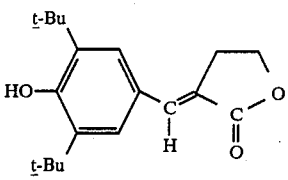

α-(3,5-di-t-butyl-4-hydroxy-benzylidine)-γ-butyrolactone

[Hidaka, et al., *Ensho*, 3(4): 511–512 (1983)]; 2,6-di-t-butyl-phenols with a heterocyclic group at the 4-position, such as:

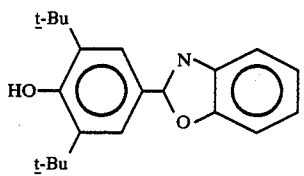

2-(3,5-di-t-butyl-4-hydroxyphenyl)benzoxazole

[Isomura, et al., *Chem. Pharm. Bull.*, 31(9): 3168–3178 (1983)];

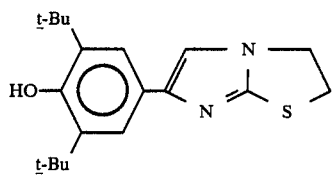

6-(3,5-di-t-butyl-4-hydroxyphenyl)-2,3-dihydroimidozo-[2,1-b]thiazole,

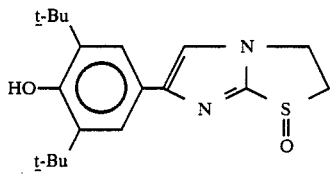

6-(3,5-di-t-butyl-4-hydroxyphenyl)-2,3-dihydroimidazo-[2,1-b]thiazole 1-oxide, and the corresponding 1,1-dioxide [Isomura, et al., *Chem. Pharm. Bull.*, 31(9): 3179–3185 (1983)]; and 3-(3,5-di-t-butyl-4-hydroxyphenyl)-2-methylpyrrole

[Isomura, et al., *Chem. Pharm. Bull.*, 32(1): 152–165 (1984)]. The compound of Formula VIII was, however, reported to be inactive.

U.S. Pat. No. 3,644,631 (to Pachter, et al.) discloses the generic formula:

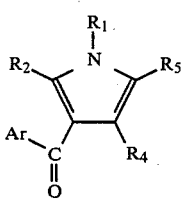
(Formula IX)

wherein, e.g., $R_1$ can be H, lower alkyl, or phenyl; $R_2$, $R_4$, and $R_5$ can be H, lower alkyl, or halo-; and Ar can be substituted aryl including tri-substituted by groups including lower alkyl or hydroxy. These compounds are proposed for anti-inflammatory uses. The disclosure, however, focuses on substitutions to the pyrrole; it does not encompass branched-chain-alkyl-substituted aryl groups, nor aryl groups with both alkyl and hydroxy substitutions.

It has been suggested that inhibition of the enzymes cyclooxygenase and lipoxygenase may be involved in the activity of anti-inflammatory agents. The involvement of antioxidant activity has also been suggested.

SUMMARY OF THE INVENTION

3-[ω-(3,5-Di-t-butyl-4-hydroxyphenyl)alkanoyl]pyrroles, their de-oxy analogs, and the pharmaceutically acceptable salts thereof, as represented by Formula X:

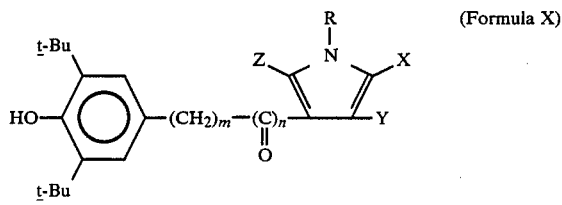
(Formula X)

wherein:
"t-Bu-" refers to $-C(CH_3)_3$, the tertiary butyl radical;
m is an integer from zero to three;
n is an integer from zero to one;
m+n is an integer from one to three;
R is H, lower alkyl, halo, carboxy lower alkylene, phenyl, benzyl, or a removable directing group; and
X, Y and Z are independently selected from H, lower alkyl, $CF_3$, halo, SCN, SR', SOR" and $SO_2R"$ (wherein R' is H, aryl, lower alkyl or lower alkanoyl; and R" is lower alkyl or aryl);
have high pharmacological potency as anti-inflammatory, analgesic and antipyretic agents, or are useful as intermediates for the synthesis of such compounds.

Compounds of Formula X are useful for the treatment of psoriasis or other allergic conditions such as conjunctivitis, bronchial asthma and inflammatory bronchial diseases, and inflammatory bone diseases, and of inflammatory diseases by virtue of the fact that they inhibit cyclooxygenase, lipoxygenase and/or the generation of superoxide radical anion.

One aspect of the present invention entails the compounds having the structure of Formula X. Another aspect of the invention entails pharmaceutical formulations of such compounds with carriers.

Yet another aspect of the invention entails processes for preparing compounds having the structure of Formula X.

Still another aspect of this invention is a method of treating pain, inflammation, pyrexia which comprises administering an effective amount of a compound having the structure of Formula X.

DETAILED DESCRIPTION OF THE PREFERRED EMBODIMENTS

Definitions

The following definitions are set forth to illustrate and define the meaning and scope of the various terms used to describe the invention herein.

As used herein, the term "alkyl" refers to an alkane radical containing only carbon and hydrogen, which is fully saturated and may be branched or straight chain.

As used herein, the term "lower alkyl" refers to an alkane radical of one to four carbon atoms, and which may be a branched or straight chain radical. This term is further exemplified by such radicals as methyl, ethyl, propyl, isopropyl, butyl, isobutyl and t-butyl.

As used herein, the term "lower alkylene" refers to a divalent fully saturated hydrocarbon radical of one to four carbon atoms, and which may be branched or straight. This term is further exemplified by such radicals as methylene, ethylene, propylene, isopropylene, butylene and isobutylene.

As used herein, the term "lower alkanoyl" refers to an alkyl carbonyl radical of the formula RC(O)—, where R is lower alkyl. This term is further exemplified by such radicals as acetyl, propanoyl and butanoyl.

As used herein, the term "carboxy lower alkylene" refers to a carboxy alkylene radical of the formula HOOC—R'—, where R' is a branched or a straight chain alkylene radical of one to three carbon atoms. This term is further exemplified by such radicals as carboxymethyl, carboxyethyl, 3-carboxypropyl and 1-methyl-2-carboxyethyl.

As used herein, the term "aryl" refers to an organic radical derived from an aromatic hydrocarbon by the removal of one hydrogen atom from the aromatic ring. The term is exemplified by phenyl, naphthyl or anthracenyl.

As used herein, the term "aryl lower alkyl" refers to a radical of the formula Ar—R—, where Ar is aryl and R is alkyl, as defined above. The term is exemplified by benzyl and phenethyl.

As used herein, the term "t-butyl" and "t-Bu-" refer to $-C(CH_3)_3$, the tertiary butyl radical.

As used herein, the term "halo" refers to bromo, iodo and chloro.

As used herein, the term "removable directing group" refers to a group that directs the acylation by an acid halide to the 3 (or beta) position of a pyrrole, and is removable thereafter under conditions that do not affect other substituents on the molecule. Such groups include electron withdrawing groups such as arylsulfonyl (e.g., phenylsulfonyl), aryl lower alkylsulfonyl (e.g., benzylsulfonyl), lower alkyl arylsulfonyl (e.g., tolylsulfonyl), lower alkylsulfonyl (e.g., ethylsulfonyl), and benzoyl. Presently preferred are arylsulfonyl, aryl lower alkylsulfonyl, lower alkyl arylsulfonyl and lower alkylsulfonyl, especially arylsulfonyl, and particularly N-phenylsulfonyl.

The compounds of Formula X are described herein as 3-[ω-(3,5-di-t-butyl-4-hydroxyphenyl)alkanoyl]pyrroles and their de-oxy analogs. This is intended to refer to an ω-(3,5-di-t-butyl-4-hydroxyphenyl)alkanoyl or an ω-(3,5-di-t-butyl-4-hydroxyphenyl)alkyl substituent at the beta position of the pyrrole ring. Thus, some substituted compounds of Formula X may be named as 4-[ω-(3,5-di-t-butyl-4-hydroxyphenyl)alkanoyl]- or 4-[ω-(3,5-di-t-butyl-4-hydroxyphenyl)alkyl]pyrroles, depending upon the nature and placement of other substituents on the pyrrole ring, for example, 2-chloro-4-(3,5-di-t-butyl-4-hydroxybenzoyl)pyrrole.

A pharmaceutically acceptable salt may be any salt derived from an inorganic or organic base which retains the activity of the parent compound and is non-toxic to a subject. Salts may be derived from such inorganic ions as sodium, potassium, lithium, ammonium, calcium, magnesium, ferrous, zinc, copper, manganous, aluminum, ferric, manganic salts and the like. Particularly preferred are the ammonium, potassium, sodium, calcium and magnesium salts. Pharmacetically acceptable salts derived from organic bases include salts of primary, secondary and tertiary amines, substituted amines including naturally occurring substituted amines, cyclic amines and basic ion exchange resins, such as isopropyl amine, trimethyl amine, diethyl amine, triethyl amine, tripropyl amine, ethanolamine, 2-dimethylaminoethanol, 2-diethylaminoethanol, tromethamine, dicyclohexylamine, lysine, arginine, histidine, caffeine, procaine, hydrabamine, choline, betaine, ethylendiamine, glucosamine, methylglucamine, theobromine, purines, piperizine, piperidine, n-ethylpiperidine, polyamine resins, and the like. Particularly preferred organic bases are isopropylamine, diethylamine, ethanolamine, piperidine, tromethamine, dicyclohexylamine, choline and caffeine.

Synthesis of the Compounds

3-[ω-(3,5-Di-t-butyl-4-hydroxyphenyl)alkanoyl]-pyrroles and their de-oxy analogs having the general structure of Formula X can be synthesized by a variety of reaction sequences, for example, in the manner shown in Sections A–N below.

Typically, the compounds of this invention can be prepared from an acid halide and an appropriately substituted or unsubstituted pyrrole starting material having a removable directing group, in accordance with the reaction sequences described below. An electron-attracting substitutent on the 2 position of a pyrrole could be used to direct addition of the acid halide to the 3 position of the pyrrole. Compounds having strongly electron-attracting substituents (such as, SOR", and SO$_2$R") are prepared from the unsubstituted 3,5-di-t-butyl-4-hydroxyphenyl -alkanoyl or -alkyl pyrrole at the end of the process, as described more fully below. On the other hand, the alkyl-substituted pyrroles (other than N-alkyl) and the trifluoromethyl-substituted pyrroles must be prepared using an alkyl- or trifluoromethyl-substituted starting material.

In the following preparations, unless specified to the contrary, the reactions take place at atmospheric pressure over a temperature range from about 0° C. to about 100° C., more preferably from about 10° C. to about 50° C., and most preferably at about room temperature.

A. Preparation of Intermediates

Referring to Reaction Scheme A, compound "C" is prepared by a Friedel-Crafts reaction between an acid halide "A" and an N-(removable directing group)pyrrole "B". As used in Reaction Scheme A, substituents X, Y and Z on "B" and "C" are not strongly electron-attracting (e.g., they can be H, lower alkyl, CF$_3$, halo, SCN or SR').

The acid halides "A" [e.g., 3,5-di-t-butyl-4-hydroxybenzoyl chloride, 3,5-di-t-butyl-4-hydroxyphenylacetyl chloride or 3-(3,5-di-t-butyl-4-hydroxyphenyl)propanoyl chloride; preferably 3,5-di-t-butyl-4-hydroxybenzoyl chloride] are obtained by halogenation of a corresponding acid (e.g., 3,5-di-t-butyl-4-hydroxybenzoic acid—available from Aldrich Chemical Company), for example by contacting it with thionyl chloride, as is known in the art.

The N-(removable directing group)pyrroles "B" (e.g., N-phenylsulfonylpyrrole, N-p-tolylsulfonylpyrrole, N-methylsulfonylpyrrole or N-phenylsulfonyl-2,5-dimethylpyrrole; preferably N-phenylsulfonylpyrrole) are also obtained by methods known in the art. For example, pyrrole, an alkyl-substituted pyrrole, a trifluoromethyl-substituted pyrrole, or a halo-substituted pyrrole [e.g., 2,5-dimethylpyrrole (available from Aldrich Chemical Company), 2-trifluoromethylpyrrole (prepared as described in Section E, below) or 2-chloropyrrole (prepared by halogenation as described in Section L, below)] is contacted with either (a) potassium in tetrahydrofuran ("THF") and then with the chloride of a removable directing group (e.g., benzylsulfonyl chloride or tolylsulfonyl chloride), or (b) sodium hydride in dimethylformamide ("DMF") and then with the chloride of a removable directing group (e.g., phenylsulfonyl chloride).

Both "A" and "B" are dissolved in an organic solvent that is inert under the conditions of the reaction (e.g., nitrobenzene, dichloromethane, dichloroethane or nitromethane; preferably dichloroethane), in the presence of an excess of a Lewis acid catalyst (e.g., aluminum trichloride, boron trifluoride, stannic chloride or ferric chloride; preferably aluminum trichloride). The Friedel-Crafts reaction takes place over a period of about 30 minutes to about 24 hours, more preferably about 45 minutes to about 4 hours, and most preferably about 1.5 hours. The resulting product "C" is conventionally isolated and purified.

For example, using 3,5-di-t-butyl-4-hydroxybenzoyl chloride and N-phenylsulfonylpyrrole in the above general reaction yields N-phenylsulfonyl-3-(3,5-di-t-butyl-4-hydroxybenzoyl)pyrrole (a compound according to Formula X wherein: m is 0; n is 1; R is SO$_2$φ; and X, Y and Z are each H). Likewise, using 3,5-di-t-butyl-4-hydroxybenzoyl chloride and N-phenylsulfonyl-2,5-dimethylpyrrole in the above general reaction yields N-phenylsulfonyl-2,5-dimethyl-3-(3,5-di-t-butyl-4-hydroxybenzoyl)pyrrole (a compound according to Formula X wherein: m is 0; n is 1; R is SO$_2$φ; Y is H; and X and Z are each CH$_3$).

Reaction Scheme A

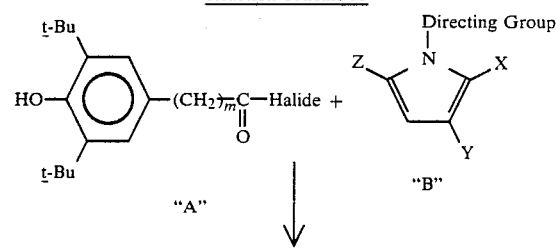

-continued
Reaction Scheme A

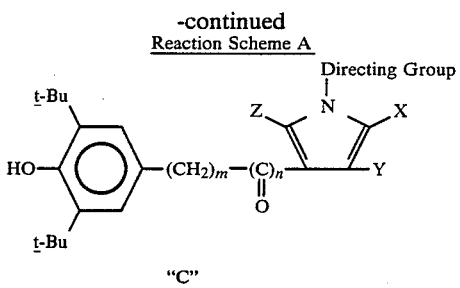

"C"

B. Preparation of Parent Compound(s)

As shown in Reaction Scheme B (where X, Y and Z can be H, lower alkyl, $CF_3$, halo, SCN or SR') the removable directing group is removed from the intermediates represented by the formula "C". This is done by dissolving a compound according to formula "C" in an organic solvent that is miscible with water and is inert under the conditions of the reaction [e.g., dioxane, methanol, nitromethane, THF, ethanol, isopropanol or acetonitrile; preferably dioxane and methanol) and adding a strong base (e.g., NaOH, KOH, or LiOH; preferably NaOH) as an aqueous solution. The reaction takes place at elevated temperatures of 40°–100° C., e.g., on a steam bath, over a period of about 5 minutes to about 1 hour, more preferably about 20 minutes. The resulting products, compounds according to formula "D", are conventionally isolated and purified.

Reaction Scheme B

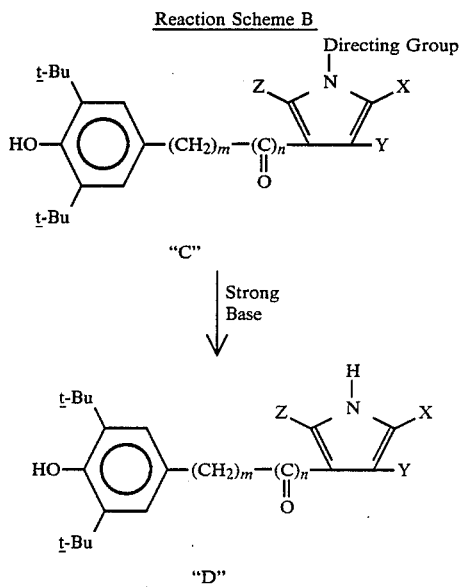

For example, using N-phenylsulfonyl-3-(3,5-di-t-butyl-4-hydroxybenzoyl)pyrrole in this general reaction yields 3-(3,5-di-t-butyl-4-hydroxybenzoyl)pyrrole (a compound according to Formula X wherein: m is 0; n is 1; R is H; and X, Y and Z are each H). Likewise, using N-phenylsulfonyl-2,5-di-methyl-3-(3,5-di-t-butyl-4-hydroxybenzoyl)pyrrole in the above general reaction yields 2,5-dimethyl-3-(3,5-di-t-butyl-4-hydroxybenzoyl)pyrrole (a compound according to Formula X wherein: m is 0; n is 1; R is H; Y is H; and X and Z are each methyl).

C. Alkylation/Benzylation of the Pyrrole's Nitrogen

As shown in Reaction Scheme C, conversion of the compounds according to formula "E" (i.e., compounds of Formula X where R is hydrogen) to the corresponding compounds according to formula "F" where R is lower alkyl or benzyl is effected by contacting the compounds "E" [dissolved in a solvent inert under the conditions of the reaction, e.g., DMF, THF, N-methylpyrrolidone, or dimethylsulfoxide ("DMSO"); preferably DMF] with about 1 to 4, preferably about 2, molar equivalents of an alkali metal hydride (e.g., KH, NaH, or LiH; preferably NaH) for about 15 minutes to about 6 hours, preferably about 1 hour.

This is followed by the addition of about 1 to 5, preferably about 1.1, molar equivalents of an alkylating agent ["R—X" where R is alkyl, benzyl or carboxy(-lower alkyl) and X is a leaving group] dissolved in the same solvent. In particular, "R—X" can be either a lower alkyl halide (e.g., methyl iodide, ethyl bromide, propyl iodide, butyl chloride), an optionally ring-substituted benzyl halide (e.g., benzyl chloride, benzyl iodide, benzyl bromide or benzyl fluoride), or a halogenated alkanoic acid or ester (e.g., chloropropionic acid, ethyl chloroacetate or preferably bromoacetic acid; these require an additional molar equivalent of the alkali metal hydride described above).

A temperature range from about −10° C. to about 50° C., preferably about room temperature can be used. The reaction takes place over a period of about 15 minutes to about 24 hours, perferably over a period of about 30 minutes to about 3 hours, and most preferably about 1 hour. The resulting product "F", in which R is lower alkyl, benzyl or carboxy lower alkylene, is conventionally isolated and purified.

Reaction Scheme C

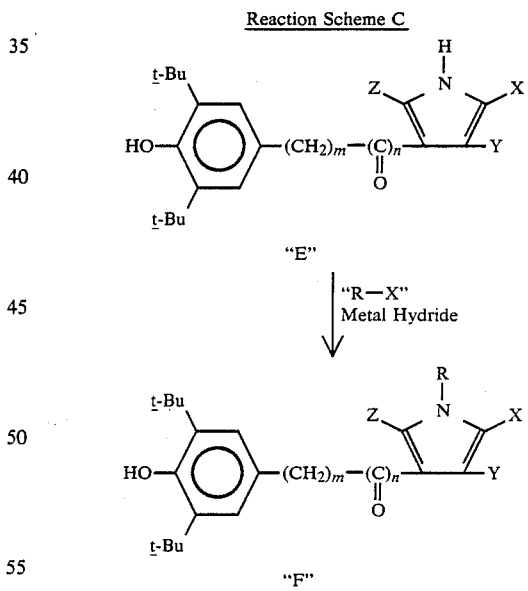

For example, using 3-(3,5-di-t-butyl-4-hydroxybenzoyl)pyrrole as compound "E" in this general reaction together with ethyl bromide as "R—X" yields N-ethyl-3-(3,5-di-t-butyl-4-hydroxybenzoyl)pyrrole (a compound according to Formula X wherein: m is 0; n is 1; R is ethyl; and X, Y and Z are each H).

Likewise, using 2,5-dimethyl-3-(3,5-di-t-butyl-4-hydroxybenzoyl)pyrrole as compound "E" in this general reaction with benzyl chloride as "R—X" yields N-benzyl-2,5-dimethyl-3-(3,5-di-t-butyl-4-hydroxybenzoyl)pyrrole (a compound according to Formula X wherein: m is 0; n is 1; R is benzyl; Y is H; and X and Z are each methyl).

Similarly, using 3-(3,5-di-t-butyl-4-hydroxybenzoyl)pyrrole as compound "E" in this general reaction with bromoacetic acid as "R—X" and 3 molar equivalents of NaH yields N-carboxymethyl-3-(3,5-di-t-butyl-4-hydroxybenzoyl)pyrrole (a compound according to Formula X wherein: m is 0; n is 1; R is CH₂COOH; and X, Y and Z are each H).

D. Alkylation of the Pyrrole Starting Material

The compounds of Formula X wherein X, Y and/or Z are lower alkyl are prepared by a Friedel-Crafts reaction, such as that described in Sections A and B above, between an acid halide and an N-(removable directing group)-(alkyl-substituted)pyrrole (e.g., N-phenylsulfonyl-2,5-dimethylpyrrole, N-phenylsulfonyl-3-ethylpyrrole or N-phenylsulfonyl-2-propylpyrrole, which are made according to methods commonly known in the art).

The N-(removable directing group)-alkyl-substituted pyrrole is prepared as described in Section A above, and is then used as compound "B" in the Friedel-Crafts reaction to give the desired end products, using the reaction times and conditions as described above.

E. Trifluoromethylation of the Pyrrole Starting Material

The compounds of Formula X wherein X, Y and/or Z are CF₃ are prepared by a Friedel-Crafts reaction, such as that described in Sections A and B above, between an acid halide and an N-(removable directing group)-(trifluoromethyl-substituted)pyrrole [e.g., N-phenylsulfonyl-2-(trifluoromethyl)pyrrole].

The pyrrole starting material may be obtained by photochemical trifluoromethylation of pyrrole, e.g., by following the procedure of Kobayashi, Y., et al., *Chem. Pharm. Bull.*, 26(4) 1247-1249 (1978). This can be accomplished by sealing CF₃I and pyrrole in a silica tube under vacuum and irradiating the sealed tube with a low pressure mercury lamp for about 2 days. After irradiation, the gaseous products are degassed at room temperature and the residue is distilled with a vacuum line, yielding the desired (trifluoromethyl)pyrrole.

F. Introduction of a Thiocyano Group on the Pyrrole Nucleus

The compounds of Formula X wherein X, Y and/or Z are —SCN, are prepared by contacting an appropriate pyrrol-3-yl ketone (i.e., a compound according to Formula X wherein X, Y and/or Z are H and R is not a removable directing group) with thiocyanogen (prepared from an alkali metal thiocyanate, such as potassium thiocyanate and bromine at 0° C. in methanol) in an organic solvent inert under the conditions of the reaction (e.g., anhydrous DMF, a lower alcohol such as methanol or ethanol, or methylene chloride). The molar ratio of thiocyanogen to starting material is about 1–10 molar equivalents, preferably about 1:1 for the monosubstituted pyrroles and in increasing ratios for the di-and tri-substituted pyrroles. The reaction takes place over a period of about 10 minutes to about 10 hours, more preferably about 30 minutes to about 4 hours, and most preferably over 1.5 hours. A temperature range from about −100° C. to about 40° C. can be used, preferably about −35° C. The end products are separated and purified by conventional means.

For example, using 3-(3,5-di-t-butyl-4-hydroxybenzoyl)pyrrole in this general reaction together with one molar equivalent of thiocyanogen yields 2-thiocyano-4-(3,5-di-t-butyl-4-hydroxybenzoyl)pyrrole (a compound according to Formula X wherein: m is 0; n is 1; R is H; and X is SCN; and Y and Z are each H).

G. Introduction of a Mercapto Group on the Pyrrole Nucleus

The compounds of Formula X wherein X, Y and/or Z are mercapto are prepared by dissolving a mono-, di- or tri-thiocyanopyrrole (prepared as described in Section F) in a protic solvent (e.g., EtOH, PrOH, t-BuOH, THF—H₂O or preferably MeOH). A methanolic solution of an inorganic base (e.g., LiOH, KOH, or preferably NaOH) is added slowly, maintaining the temperature of the reaction mixture between about −30° C. to about 5° C., preferably about −10° C. After mechanical agitation (e.g., stirring) for a period of about 5 minutes to about 3 hours, preferably about 1 hour, an excess of an acidifying agent (e.g., 20% HCl) is added, yielding the desired mercaptopyrrole, which is purified and isolated by conventional means.

For example, using 2-thiocyano-4-(3,5-di-t-butyl-4-hydroxybenzoyl)pyrrole in this general reaction together with one molar equivalent of potassium hydroxide yields 2-mercapto-4-(3,5-di-t-butyl-4-hydroxybenzoyl)pyrrole (a compound according to Formula X wherein: m is 0; n is 1; R is H; and X is SH; and Y and Z are each H).

H. Introduction of an Alkylthio Group on the Pyrrole Nucleus

The compounds of Formula X wherein X, Y and/or Z are lower-alkylthio, are prepared by contacting a mono-, di- or tri-thiocyanopyrrole (prepared as described in Section F) with an alkyl halide ("R—X", as defined earlier; preferably an alkyl iodide such as methyl iodide or ethyl iodide) in the corresponding protic solvent ("R—OH", e.g., MeOH, EtOH, PrOH; preferably MeOH). Alternatively, t-BuOh or THF—H₂O can be used as the solvent. The molar ratio of alkyl halide to starting material will vary (i.e., 1:1, 2:1 or 3:1) depending upon whether a mono-, di-, or tri-substituted product is desired. The reaction mixture is then cooled to about −30° C. to about 5° C., preferably about −5° C., and a methanolic solution of an inorganic base (e.g., LiOH, KOH, or preferably NaOH) is added. The mixture is brought to about 0° C. to about 40° C., preferably about room temperature, and the mixture is allowed to react for a period of about 5 minutes to about 4 hours, preferably about 30 minutes. The solution is neutralized with dry-ice. The end products are purified and isolated by conventional means.

For example, using 2,3-dithiocyano-4-(3,5-di-t-butyl-4-hydroxybenzoyl)pyrrole in this general reaction together with two molar equivalents of methyl iodide yields 2,3-dimethylthio-4-(3,5-di-t-butyl-4-hydroxybenzoyl)pyrrole (a compound according to Formula X wherein: m is 0; n is 1; R is H; and Z is H; and X and Y are each SCH₃).

Alternatively, the compounds of Formula X where X, Y and/or Z are lower-alkylthio may be prepared by contacting an acylated pyrrole (dissolved in a solvent such as DMF) with a solution of an alkyl or aryl sulfenyl chloride, previously prepared from a mixture of an alkyl or aryl disulfide (e.g., methyl disulfide) and sulfuryl chloride in an inert organic solvent (e.g., CCl₄, CHCl₃ or CH₂Cl₂). The molar ratio of sulfenyl chloride to starting material will vary (i.e., 1:1, 2:1 or 3:1) depending upon whether a mono-, di-, or tri-substituted product is desired. The reaction takes place in about 30 minutes to about 4 hours, preferably about 1 hour. The end products are purified and isolated by conventional means.

I. Introduction of a Lower-Alkanoylthio Group on the Pyrrole Nucleus

The compounds of Formula X wherein X, Y and/or Z are lower-alkanoylthio, are prepared by contacting a mono-, di- or tri-thiocyanopyrrole (prepared as described in Section F) with an alkali metal acetate (e.g., potassium acetate, or preferably sodium acetate) and dissolving in an alkanoic acid (e.g., propanoic acid, or preferably acetic acid) and an alkanoic anhydride (e.g., propionic anhydride, or preferably acetic anhydride). With vigorous mechanical agitation (e.g., stirring), a strong reducing agent, preferably zinc dust, is added. The reaction mixture is neutralized with ice water. The mixture is allowed to react for a period of about 30 minutes to about 8 hours, preferably about 3 hours. The end product is isolated and purified by conventional means.

For example, using 2-thiocyano-4-(3,5-di-t-butyl-4-hydroxybenzoyl)pyrrole in this general reaction together with one molar equivalent each of sodium acetate, acetic acid, acetic anhydride and zinc dust, yields 2-acetylthio-4-(3,5-di-t-butyl-4-hydroxybenzoyl)pyrrole (a compound according to Formula X wherein: m is 0; n is 1; R is H; and X is SAc; and Y and Z are each H).

J. Introduction of an Alkylsulfinyl Group on the Pyrrole Nucleus

The compounds of Formula X wherein X, Y and/or Z are —SOR", are prepared by the oxidation of an appropriate alkylthiopyrrol-3-yl ketone (prepared as described in Section H), which is carried out with one molar equivalent of an oxidizing agent (e.g., 30% hydrogen peroxide, peracetic acid, or preferably m-chloroperbenzoic acid) for each alkylthio group on the starting molecule, in an organic solvent inert under the conditions of the reaction (e.g., $CHCl_3$, $CCl_4$, acetone or preferably dichloromethane). The reaction takes place over a period of about 10 minutes to about 2 hours, more preferably 20 minutes to about 1 hour, and most preferably over about 30 minutes after the addition of the oxidizing agent. A temperature range from about 0° C. to about 50° C., more preferably from about −20° C. to about 10° C., and most preferably 0° C. may be used. The end products are isolated and purified by conventional means.

For example, using 2,5-dimethylthio-4-(3,5-di-t-butyl-4-hydroxybenzoyl)pyrrole in this general reaction together with two molar equivalents of m-chloroperbenzoic acid yields 2,5-dimethylsulfinyl-4-(3,5-di-t-butyl-4-hydroxybenzoyl)pyrrole (a compound according to Formula X wherein: m is 0; n is 1; R is H; Y is H; and X and Z are each $SOCH_3$).

K. Introduction of an Alkylsulfonyl Group on the Pyrrole Nucleus

The compounds of Formula X wherein X, Y and/or Z are $SO_2R''$, are prepared by the oxidation of an appropriate alkylsulfinylpyrrol-3-yl ketone (prepared as described in Section J), which is carried out with one molar equivalent of an oxidizing agent (preferably m-chloroperbenzoic acid) for each alkylsulfinyl group on the starting molecule, in an inert organic solvent (e.g., dichloromethane). Alternatively, the reaction can be carried out starting with an appropriate alkylthiopyrrol-3-yl ketone (prepared as described in Section H), with two molar equivalents of oxidizing agent per —SR'. The reaction takes place over a period of about 10 minutes to about 2 hours, more preferably 20 minutes to about 1 hour, and most preferably over about 30 minutes after the addition of the oxidizing agent. The end products are purified by conventional means.

For example, using 2-methylsulfinyl-4-[2-(3,5-di-t-butyl-4-hydroxyphenyl)-1-oxo-ethyl]pyrrole in this general reaction together with one molar equivalent of m-chloroperbenzoic acid yields 2-methylsulfonyl-4-[2-(3,5-di-t-butyl-4-hydroxyphenyl)-1-oxo-ethyl]pyrrole (a compound according to Formula X wherein: m is 1; n is 1; R is H; and X is $SO_2CH_3$; and Y and Z are each H).

L. Introduction of a Halo Group on the Pyrrole Nucleus

As an alternative to starting with the halogenated pyrroles as described in Sections A & B above, the compounds of Formula X wherein X, Y and/or Z are halo and the other substituents are as described, can also be prepared by the halogenation of an appropriate pyrrole (such as a compound according to Formula X in which X, Y and/or Z is hydrogen and the other substituents are as described above). The reaction is carried out with a halogenating agent in an organic solvent that is inert under the conditions of the reaction (e.g., anhydrous methylene chloride, carbon tetrachloride, or trichloromethane; preferably anhydrous methylene chloride). The molar ratio of halogenating agent to starting material will vary (e.g., 1:1, 2:1 or 3:1) depending, respectively, upon whether a mono-, di-, or tri-substituted end product is desired. The end products are purified and isolated by conventional means. Alternatively, the starting material may be reacted with in excess of 4:1 molar equivalents of halogenating agent to form a stable tetrahalo intermediate, followed by dehalogenation of the N-halo substituent.

To prepare the compounds of Formula X where the substituents X, Y and/or Z are chloro, the halogenating agent is, e.g., elemental chlorine, N-chlorosuccinimide, 1,3-dichloro-5,5-dimethylhydantoin or preferably sulfuryl chloride. The reaction takes place over a period of about 10 minutes to about 4 hours, preferably about 20 minutes to about 1 hour, and most preferably about 30 minutes. Proceeding via the tetrachloro intermediate requires cooling the initial reactants to about −50° to about −100° C., preferably about −70° C., and allowing the reaction to run for about 6 to about 24 hours, preferably about 20 hours; this is followed by removal of the N-chloro substituent by treatment with a dehalogenating agent, such as a metal halide (e.g., potassium iodide) and a metal sulfite (e.g., sodium sulfite).

For example, using 3-(3,5-di-t-butyl-4-hydroxybenzoyl)pyrrole in this general reaction together with one molar equivalent of 1,3-dichloro-5,5-dimethylhydantoin as the halogenating agent yields 2-chloro-4-(3,5-di-t-butyl-4-hydroxybenzoyl)pyrrole (a compound according to Formula X wherein: m is 0; n is 1; R is H; X is Cl; and Y and Z are each H).

Using 3-(3,5-di-t-butyl-4-hydroxybenzoyl)pyrrole in this general reaction together with over four molar equivalents of sulfuryl chloride as the halogenating agent yields 1,2,4,5-tetrachloro-3-(3,5-di-t-butyl-4-hydroxybenzoyl)pyrrole (a compound according to Formula X wherein: m is 0; n is 1; and R, X, Y and Z are each Cl). Treatment of this tetrachloro intermediate with potassium iodide and sodium sulfite in water yields 2,4,5-trichloro-3-(3,5-di-t-butyl-4-hydroxybenzoyl)pyrrole (a compound according to Formula X wherein: m is 0; n is 1; R is H; and X, Y and Z are each Cl).

To prepare the compounds of Formula X where the substituents X, Y and/or Z are bromo, the halogenating agent is, e.g., N-bromosuccinimide or preferably elemental bromine. The reaction takes place over a period of about 30 minutes to about 4 hours, more preferably about 45 minutes to about 2 hours, and most preferably about 1 hour. A temperature range of about −100° C. to about −50° C., preferably about −70° C. may be used.

For example, using N-benzyl-3-(3,5-di-t-butyl-4-hydroxybenzoyl)pyrrole in this general reaction together with two molar equivalents of elemental bromine as the halogenating agent yields N-benzyl-2,3-dibromo-4-(3,5-di-t-butyl-4-hydroxybenzoyl)pyrrole (a compound according to Formula X wherein: m is 0; n is 1; R is benzyl; X and Y are Br; and Z is H).

To prepare the compounds of Formula X where the substituents X, Y and/or Z are iodo, the halogenating agent is, e.g., iodosuccinimide or preferably elemental iodine. The reaction takes place at atmospheric pressure over a period of about 30 minutes to about 4 hours, more preferably about 45 minutes to about 2 hours, and most preferably about 1 hour.

For example, using N-methyl-3-(3,5-di-t-butyl-4-hydroxybenzoyl)pyrrole in this general reaction together with one molar equivalent of elemental iodine as the halogenating agent yields N-methyl-2-iodo-3-(3,5-di-t-butyl-4-hydroxybenzoyl)pyrrole (a compound according to Formula X wherein: m is 0; n is 1; R is methyl; X and Y are H; and Z is I).

M. Reduction of Oxo Pyrroles

Compounds of Formula X where n is 0 can be prepared by the reduction of a 3-[ω-(3,5-di-t-butyl-4-hydroxyphenyl)-1-oxo-alkyl]pyrrole (e.g., a compound according to Formula X wherein n is 1) by contacting it with an excess (about 8:1 molar equivalents) of a strong reducing agent [e.g., lithium borohydride, sodium borohydride, or preferably lithium aluminum hydride ("LAH")] in an ethereal solvent (e.g., ether, dioxane or preferably THF). The reaction takes place in a temperature range from about 20° C. to about 100° C., more preferably from about 40° C. to about 80° C., and most preferably at about 65° C. (or the reflux temperature for the solvent being used). The reaction takes place over a period of about 1–10 hours, more preferably 2–6 hours, and most preferably 4 hours. The product is purified and isolated by conventional means.

For example, using 2-methylsulfonyl-4-[2-(3,5-di-t-butyl-4-hydroxyphenyl)-1-oxo-ethyl]pyrrole in this generation reaction together with eight molar equivalents of LAH yields 2-methylsulfonyl-4-[2-(3,5-di-t-butyl-4-hydroxyphenyl)ethyl]pyrrole (a compound according to Formula X wherein: m is 2; n is 0; R is H; and X is $SO_2CH_3$; and Y and Z are each H). Likewise, using 3-(3,5-di-t-butyl-4-hydroxybenzoyl)pyrrole in this general reaction together with eight molar equivalents of LAH yields 3-(3,5-di-t-butyl-4-hydroxybenzyl)pyrrole (a compound according to Formula X wherein: m is 1; n is 0; R is H; and X, Y and Z are each H).

Alternatively, the compounds of Formula X where n is 0 can be prepared according to general reactions described in Sections C–E (i.e., excepting the electron withdrawing group-substituted pyrroles) using a 3-[ω-(3,5-di-t-butyl-4-hydroxyphenyl)alkyl]pyrrole [e.g., 3-(3,5-di-t-butyl-4-hydroxybenzyl)pyrrole] as the starting material, which is prepared as described above.

N. Preparation of the Pharmaceutically Acceptable Salts

The pharmaceutically acceptable salts are formed on any or a combination of the following acidic sites in the compounds of Formula X, including the hydroxy radical of the phenol, the N-hydrogen of the pyrrole when R is hydrogen, the carboxyl when R is carboxy lower alkylene, or the hydrogen of —SH when X, Y and/or Z is mercapto.

In general, these salts are formed by dissolving a compound of Formula X in a solvent that is inert under the conditions of the reaction (e.g., a protic solvent such as aqueous alcohol, alcohol, or a dipolar aprotic solvent such as acetonitrile, dimethylformamide or dimethylsulfoxide; preferably ethanol or aqueous ethanol for inorganic bases; and for the organic bases, e.g., methylene chloride) and contacting the dissolved compound with one molar equivalent of the chosen inorganic ion or organic base, as described previously, for each salt forming site to be reacted. The reaction typically takes place over a period of about 5 minutes to about 2 hours, preferably about 30 minutes.

As is well known in the art, the salts, once formed, may be interconverted with other salts or released to form the free compound.

Preferred Compounds

A presently preferred compound is 3-(3,5-di-t-butyl-4-hydroxybenzoyl)pyrrole [or 2,6-di(t-butyl)-4-(3-pyrroloyl)phenol], as shown in Formula XI).

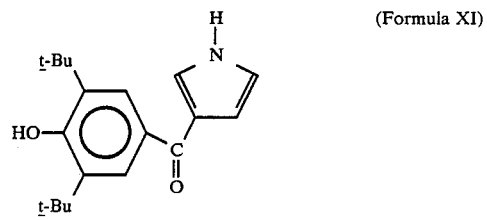
(Formula XI)

3-(3,5-Di-t-butyl-4-hydroxybenzoyl)pyrrole is both an active anti-inflammatory agent and an intermediate for synthesizing other compounds according to Formula X. Other presently preferred compounds include: 2-chloro-4-(3,5-di-t-butyl-4-hydroxbenzoyl)pyrrole; 2,4,5-trichloro-3-(3,5-di-t-butyl-4-hydroxybenzoyl)pyrrole, and 2-thiocyano-4-(3,5-di-t-butyl-4-hydroxybenzoyl)pyrrole.

As shown in Sections A & B above, compound "D" is prepared through an intermediate "C". N-Phenylsulfonyl-3-(3,5-di-t-butyl-4-hydroxybenzoyl)pyrrole (shown in Formula XII) is a presently preferred N-(removable directing group)-substituted intermediate compound.

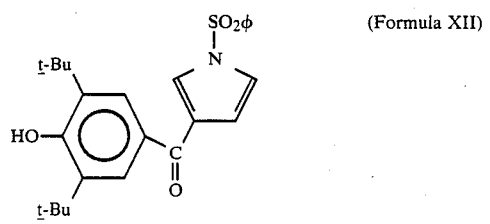
(Formula XII)

Another preferred intermediate is 1,2,4,5-tetrachloro-3-(3,5-di-t-butyl-4-hydroxybenzoyl)pyrrole.

Preferred Processes of the Invention

The compounds of the present invention can be prepared according to the following last steps.

A preferred process for preparing the compounds of the invention involves a Friedel-Crafts reaction wherein a 3,5-di-t-butyl-4-hydroxyphenyl acid halide is directed to attach to the 3-position of pyrrole. A removable directing group (such as a alkylsulfonyl, phenylsulfonyl or tolylsulfonyl) is substituted on the pyrrole's nitrogen atom before the Friedel-Crafts reaction, and is later removed. The Friedel-Crafts reaction is also performed with an alkyl-, a trifluoromethyl- or a halo-substituted pyrrole to give the corresponding alkyl-, trifluoromethyl- or halo-substituted end product of Formula X.

Other substituted compounds can be prepared as follows:

alkylation of the pyrrole's nitrogen;

carboxyalkylation of the pyrrole's nitrogen;

halogenation of the 2, 3 and/or 5 carbon atoms of the pyrrole;

reduction of the N-halo of a 1,2,4,5-tetrahalo-3-(3,5-di-t-butyl-4-hydroxybenzoyl)pyrrole;

thiocyanogenation of the 2, 3 and/or 5 carbon atoms of the pyrrole;

thiocyanogenation of the 2, 3 and/or 5 carbon atoms of an N-substituted pyrrole;

forming a mercapto radical on the 2, 3 and/or 5 carbon atoms by alkaline hydrolysis and subsequent acidification of a 2-, 3- and/or 5-thiocyanopyrrole;

forming a mercapto radical on the 2, 3 and/or 5 carbon atoms by alkaline hydrolysis and subsequent acidification of an N-substituted 2-, 3- and/or 5-thiocyanopyrrole;

alkylation of the sulfur on the 2, 3 and/or 5 carbon atoms of a 2-, 3- and/or 5-thiocyanopyrrole to form an alkylthio radical;

alkylation of the sulfur on the 2, 3 and/or 5 carbon atoms of an N-substituted a 2-, 3- and/or 5-thiocyanopyrrole to form an alkylthio radical;

oxidation of the sulfur on the 2, 3 and/or 5 carbon atoms of a 2-, 3- and/or 5-alkylthiopyrrole to form a corresponding 2-, 3- and/or 5-alkylsulfinylpyrrole;

oxidation of the sulfur on the 2, 3 and/or 5 carbon atoms of an N-substituted 2-, 3- and/or 5-alkylthiopyrrole to form a corresponding N-substituted 2-, 3- and/or 5-alkylsulfinylpyrrole;

oxidation of the sulfur on the 2, 3 and/or 5 carbon atoms of a 2-, 3- and/or 5-alkylthiopyrrole to form a corresponding 2-, 3- and/or 5-alkylsulfonylpyrrole;

oxidation of the sulfur on the 2, 3 and/or 5 carbon atoms of an N-substituted 2-, 3- and/or 5-alkylthiopyrrole to form a corresponding N-substituted 2-, 3- and/or 5-alkylsulfonylpyrrole;

oxidation of the sulfur on the 2, 3 and/or 5 carbon atoms of a 2-, 3- and/or 5-alkylsulfinylpyrrole to form a corresponding 2-, 3- and/or 5-alkylsulfonylpyrrole;

oxidation of the sulfur on the 2, 3 and/or 5 carbon atoms of an N-substituted 2-, 3- and/or 5-alkylsulfinylpyrrole to form a corresponding N-substituted 2-, 3- and/or 5-alkylsulfonylpyrrole;

reduction of a 3,5-di-t-butyl-4-hydroxyphenyl-oxoalkylpyrrole to the corresponding 3,5-di-t-butyl-4-hydroxyphenylalkylpyrrole;

addition of pharmaceutically acceptable bases to the compounds of Formula X; and release of salts to form the free compounds of Formula X.

Isolation and purification of the compounds and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples below. However, other equivalent separation or isolation procedures can, of course, also be used.

Administration and Formulation

One aspect of the present invention relates to a pharmaceutical composition useful in the treatment of inflammatory diseases such as arthritis, which composition comprises a therapeutically effective amount of a compound of Formula X, and/or a pharmaceutically accepted salt thereof, in admixture with a pharmaceutically acceptable non-toxic carrier.

A therapeutically effective amount is that amount which, when administered to a mammal in need thereof, is sufficient to effect treatment, as described above, i.e., to reduce or otherwise treat inflammation, pain and/or pyrexia in the mammal. Daily dosages of the compounds of the present invention may range between 0.1–50.0 mg/kg of body weight, preferably in the range of 1.0–20.0 mg/kg. Optimally, a dose of 15.0 mg/kg is used.

The level of the drug in a formulation can vary within the full range employed by those skilled in the art, e.g., from about 0.01 percent weight (% w) to about 99.99% w of the drug based on the total formulation and about 0.01% w to 99.99% w excipient. Preferably the drug is present at a level of about 10% w to about 70% w.

Useful pharmaceutical carriers for the preparation of the pharmaceutical compositions hereof can be solids or liquids. Thus, the compositions can take the form of tablets, pills, capsules, powders, sustained release formulations, solutions, suspensions, elixirs, aerosols, and the like. Carriers can be selected from the various oils, including those of petroleum, animal, vegetable or synthetic origin, for example, peanut oil, soybean oil, mineral oil, sesame oil, and the like. Water, saline, aqueous dextrose, and glycols are preferred liquid carriers, particularly for injectable solutions. Suitable pharmaceutical carriers include starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the like. Other suitable pharmaceutical carriers and their formulations are described in "*Remington's Pharmaceutical Sciences*" by E. W. Martin.

Another aspect of the present invention relates to a method for treating inflammatory diseases such as arthritis in a mammalian subject, whether domestic (e.g., cattle, pigs, sheep, goats, horses), pets (e.g., cats, dogs) or preferably humans, which method comprises administering a therapeutically effective amount of a compound of Formula X to a mammal in need thereof.

In the practice of the above-described method of the present invention, a therapeutically effective amount of the compound of Formula X or a pharmaceutical composition containing same is administered via any of the usual and acceptable methods known in the art, either singly or in combination with another compound or compounds of the present invention or other pharmaceutical agents. These compounds or compositions can thus be administered orally, systemically (e.g., transdermally, intranasally or by suppository), parenterally (e.g., intramuscularly, subcutaneously and intravenously), or topically, and can be administered either in the form of solid or liquid dosages including tablets, solutions, suspensions, aerosols, and the like, as discussed in more detail above. It is preferred to administer compounds of Formula X orally.

The formulation can be administered in a single unit dosage form for continuous treatment or in a single unit dosage form ad libitum when relief of symptoms is specifically required.

Anti-inflammatory activity is determined by following tests: the Adjuvant-Induced Arthritis Assay [Pearson, *Proc. Soc. Exp. Biol. Med.*, 91: 95–101 (1956)]; the Carrageenan-Induced Rat Paw Inflammation Assay [Winter, et al., *Proc. Soc. Exp. Biol. Med.*, 111: 544–547 (1962)]; the Arachidonic Acid-Induced Mouse Ear Edema Assay [Young, et al., *J. Invest. Derm.*, 82: 367–371 (1984)]; the Phenylquinone-induced Mouse Writhing Assay [Hendershot, et al., *J. Pharmacol. Exp. Ther.*, 125: 237–240 (1959)]; and the Human Polymorphonuclear Leukocyte (HPMN) Assay [Radmark, et al., *Febs Letters*, 110(2): 213–215 (1980)].

The anti-inflammatory effectiveness of 3-(3,5-di-t-butyl-4-hydroxybenzoyl)pyrrole (Formula XI) was compared with that of 2-(3,5-di-t-butyl-4-hydroxybenzoyl)pyrrole (Formula I) by conducting the above-described assays. These assays and their results are reported in Examples 30–35 and 37. The results show that the representative compound of the present invention has demonstrated increased anti-inflammatory potency over the closest known anti-inflammatory agent. The other compounds according to Formula X also have the desired activities. All of the compounds of the present invention are quite specific as to cyclooxygenase and/or lipoxygenase inhibition and are very well tolerated, e.g., having a high $LD_{50}$, low ulcerogenicity and the like.

EXAMPLES

The following examples are given to enable those skilled in the art to more clearly understand and to practice the present invention. They should not be considered as a limitation on the scope of the invention, but merely as being illustrative and representative thereof.

EXAMPLE 1

Synthesis of N-phenylsulfonyl-3-(3,5-di-t-butyl-4-hydroxybenzoyl)-pyrrole

1A. Formula X Where R is Phenylsulfonyl 6.65 G of 3,5-di-t-butyl-4-hydroxybenzoic acid was converted into its acid chloride by suspending it in 20 ml of dry methylene chloride and reacting it with 4 g of thionyl chloride followed by 7 drops of DMF. After 20 minutes, a sample treated with methanol showed no remaining acid. The solution was evaporated to dryness, and then azeotropically distilled twice with benzene, to remove excess thionyl chloride.

The crude acid chloride was dissolved in dichloroethane (125 ml), and $AlCl_3$ (3.85 g) was added. The mixture was stirred for 10 minutes at room temperature. N-phenylsulfonylpyrrole (5.0 g) dissolved in dichloroethane (50 ml) was added. The reaction mixture was stirred at room temperature for 90 minutes, poured into a 50:50 water-methylene chloride mixture and stirred. The layers were separated and the organic solution was dried on sodium sulfate. After evaporation of the solvent to dryness, the residue was recrystallized from methanol to give 6.50 g of a white crystalline powder, identified as N-phenylsulfonyl-3-(3,5-di-t-butyl-4-hydroxybenzoyl)pyrrole, the compound of Formula XII (and a compound according to Formula X wherein: m is 0; n is 1; R is $SO_2\phi$; and X, Y and Z are H) (mp 214°–215.5°—corrected).

Analysis calculated for $C_{25}H_{29}NO_4S$ (mw 439.556): Theoretical: C, 68.31; H, 6.65; N, 3.19. Found: C, 68.34; H, 6.89; N, 3.04.

1B. Formula X Where R is Phenylsulfonyl and X, Y and/or Z are Halo or Lower Alkyl Similarly, by following the procedure of part A above and substituting for N-phenylsulfonylpyrrole the following starting materials:
N-phenylsulfonyl-3-chloropyrrole,
N-phenylsulfonyl-2-(trifluoromethyl)pyrrole,
N-phenylsulfonyl-2,5-di-methylpyrrole, and
N-phenylsulfonyl-2-ethylpyrrole;
there are obtained the following respective compounds:
N-phenylsulfonyl-3-chloro-4-(3,5-di-t-butyl-4-hydroxybenzoyl)pyrrole,
N-phenylsulfonyl-2-(trifluoromethyl)-4-(3,5-di-t-butyl-4-hydroxybenzoyl)pyrrole,
N-phenylsulfonyl-2,5-dimethyl-3-(3,5-di-t-butyl-4-hydroxybenzoyl)pyrrole, and
N-phenylsulfonyl-2-ethyl-3-(3,5-di-t-butyl-4-hydroxybenzoyl)pyrrole.

1C. Formula X Where R is a Removable Directing Group Other Than Phenylsulfonyl

Similarly, by following the procedure of part A above and substituting for N-phenylsulfonylpyrrole the following starting materials:
N-p-tolylsulfonylpyrrole,
N-methylsulfonyl-2,5-dimethylpyrrole, and
N-benzylsulfonylpyrrole;
there are obtained the following respective compounds:
N-p-tolylsulfonyl-3-(3,5-di-t-butyl-4-hydroxybenzoyl)-pyrrole [(recrys. from methanol, mp 121°–123° C.);
$^1H$ nmr: 1.48s (18H), 2.43s (3H), 5.73s (OH), 6.8m (1H), 7.25m (1H), 7.38s (1H), 7.76m (6H)],
N-methylsulfonyl-2,5-dimethyl-3-(3,5-di-t-butyl-4-hydroxybenzoyl)pyrrole, and
N-benzylsulfonyl-3-(3,5-di-t-butyl-4-hydroxybenzoyl)-pyrrole.

1D. Formula X Where R is Phenylsulfonyl, m is 1–2 and n is 1

Similarly, by following the procedure of part A above and substituting for 3,5-di-t-butyl-4-hydroxybenzoic acid the following starting materials:
3,5-di-t-butyl-4-hydroxyphenylacetic acid, and
3-(3,5-di-t-butyl-4-hydroxyphenyl)propanoic acid;
there are obtained the following respective compounds:
N-phenylsulfonyl-3-[2-(3,5-di-t-butyl-4-hydroxyphenyl)-1-oxoethyl]pyrrole, and
N-phenylsulfonyl-3-[3-(3,5-di-t-butyl-4-hydroxyphenyl)-1-oxopropyl]pyrrole.

EXAMPLE 2

Synthesis of 3-(3,5-di-t-butyl-4-hydroxybenzoyl)pyrrole

2A. Formula XI

3 G of N-phenylsulfonyl-3-(3,5-di-t-butyl-4-hydroxybenzoyl)pyrrole, a material obtained in Example I, was dissolved in dioxane (300 ml) and methanol (100 ml), and 5N sodium hydroxide (100 ml) was added. The solution was heated on steam for 20 minutes, concentrated under reduced pressure and partitioned between ether and water. The ether layer was washed once with water, dried on sodium sulfate and evaporated to dryness.

The crude solid thus obtained was taken up in methylene chloride and passed through a short alumina column (3% H₂O). The first yellow fraction was discarded, after which the desired product, 3-(3,5-di-t-butyl-4-hydroxybenzoyl)pyrrole, the compound of Formula XI (and a compound according to Formula X wherein: m is 0; n is 1; R is H; and X, Y and Z are H), came off. The solid so obtained was homogeneous on the tlc and weighed 2.0 g; it was recrystallized from ether-hexane (mp 170.5°–171.0° C.—corrected).

Analysis calculated for $C_{19}H_{25}NO_2$ (mw 299.398): Theoretical: C, 76.22; H, 8.42; N, 4.68. Found: C, 76.41; H, 8.66; N, 4.63.

2B. Formula X Where X, Y and/or Z are Halo or Lower Alkyl

Similarly, by following the procedure of part A above and substituting for N-phenylsulfonyl-3-(3,5-di-t-butyl-4-hydroxybenzoyl)pyrrole the following starting materials:
N-phenylsulfonyl-3-chloro-4-(3,5-di-t-butyl-4-hydroxybenzoyl)pyrrole,
N-phenylsulfonyl-2-(trifluoromethyl)-4-(3,5-di-t-butyl-4-hydroxybenzoyl)pyrrole,
N-phenylsulfonyl-2,5-dimethyl-3-(3,5-di-t-butyl-4-hydroxybenzoyl)pyrrole, and
N-phenylsulfonyl-2-ethyl-4-(3,5-di-t-butyl-4-hydroxybenzoyl)pyrrole;
there are obtained the following respective compounds:
3-chloro-4-(3,5-di-t-butyl-4-hydroxybenzoyl)pyrrole,
2-(trifluoromethyl)-4-(3,5-di-t-butyl-4-hydroxybenzoyl)pyrrole,
2,5-dimethyl-3-(3,5-di-t-butyl-4-hydroxybenzoyl)pyrrole, and
2-ethyl-4-(3,5-di-t-butyl-4-hydroxybenzoyl)pyrrole.

2C. Formula X Where R is a Removable Directing Group Other Than Phenylsulfonyl

Similarly, by following the procedure of part A above and substituting for N-phenylsulfonyl-3-(3,5-di-t-butyl-4-hydroxybenzoyl)pyrrole the following starting materials:
N-p-tolylsulfonyl-3-(3,5-di-t-butyl-4-hydroxybenzoyl)pyrrole,
N-methylsulfonyl-2,5-dimethyl-3-(3,5-di-t-butyl-4-hydroxybenzoyl)pyrrole, and
N-benzylsulfonyl-3-(3,5-di-t-butyl-4-hydroxybenzoyl)pyrrole;
there are obtained the following respective compounds:
3-(3,5-di-t-butyl-4-hydroxybenzoyl)pyrrole,
2,5-dimethyl-3-(3,5-di-t-butyl-4-hydroxybenzoyl)pyrrole, and
3-(3,5-di-t-butyl-4-hydroxybenzoyl)pyrrole.

2D. Formula X Where m is 1–2 and n is 1

Similarly, by following the procedure of part A above and substituting for N-phenylsulfonyl-3-(3,5-di-t-butyl-4-hydroxybenzoyl)pyrrole the following starting materials:
N-phenylsulfonyl-3-[2-(3,5-di-t-butyl-4-hydroxyphenyl)-1-oxoethyl]pyrrole, and
N-phenylsulfonyl-3-[3-(3,5-di-t-butyl-4-hydroxyphenyl)-1-oxopropyl]pyrrole;
there are obtained the following respective compounds:
3-[2-(3,5-di-t-butyl-4-hydroxyphenyl)-1-oxoethyl]pyrrole, and
3-[3-(3,5-di-t-butyl-4-hydroxyphenyl)-1-oxopropyl]pyrrole.

EXAMPLE 3

Synthesis of N-methyl-3-(3,5-di-t-butyl-4-hydroxybenzoyl)pyrrole

3A. Formula X Where R is Methyl

2 G (6.6 mmol) of 3-(3,5-di-t-butyl-4-hydroxybenzoyl)pyrrole were added to a stirred suspension of 640 mg (13 mmol) of sodium hydride (50% in mineral oil) in 20 ml of anhydrous dimethylformamide. After 1 hour at room temperature, 0.415 ml (6.68 mmol) of methyl iodide was added, and stirring at room temperature was continued for an additional hour. Nitrogen was then bubbled through the reaction mixture for 10 minutes and thereafter the reaction mixture was partitioned between methylene chloride and water. The organic phase was washed with water, dried and evaporated in vacuo. Purification of the crude product by t.l.c. using hexane:ethyl acetate (80:20) afforded 1.439 g (69%) of the title compound, which was recrystallized from methylene chloride-hexane (mp 135.5°–136.5° C.).

3B. Formula X Where R is Carboxy Lower Alkylene, Benzyl or Lower Alkyl Other Than Methyl Similarly, by following the procedure of part A above and substituting for methyl iodide the following starting materials:
bromoacetic acid (with an additional molar equivalent of NaH),
ethyl iodide,
propyl bromide,
butyl chloride, and
benzyl bromide;
there are obtained the following respective compounds:
3-(3,5-di-t-butyl-4-hydroxybenzoyl)pyrrole-N-acetic acid,
N-ethyl-3-(3,5-di-t-butyl-4-hydroxybenzoyl)pyrrole (mp 73°–75° C.),
N-propyl-3-(3,5-di-t-butyl-4-hydroxybenzoyl)pyrrole,
N-butyl-3-(3,5-di-t-butyl-4-hydroxybenzoyl)pyrrole (mp 101°–103° C.), and
N-benzyl-3-(3,5-di-t-butyl-4-hydroxybenzoyl)pyrrole (mp 123°–124° C.).

3C. Formula X Where R is Methyl, m is 1–3 and n is 0–1

Similarly, by following the procedure of part A above and substituting for 3-(3,5-di-t-butyl-4-hydroxybenzoyl)pyrrole the following starting materials:
3-(3,5-di-t-butyl-4-hydroxybenzyl)pyrrole,
3-[3-(3,5-di-t-butyl-4-hydroxyphenyl)propyl]pyrrole,
3-[2-(3,5-di-t-butyl-4-hydroxyphenyl)-1-oxoethyl]pyrrole, and
3-[3-(3,5-di-t-butyl-4-hydroxyphenyl)-1-oxopropyl]pyrrole,
there are obtained the following respective compounds:
N-methyl-3-(3,5-di-t-butyl-4-hydroxybenzyl)pyrrole,
N-methyl-3-[3-(3,5-di-t-butyl-4-hydroxyphenyl)propyl]pyrrole,
N-methyl-3-[2-(3,5-di-t-butyl-4-hydroxyphenyl)-1-oxoethyl]pyrrole, and
N-methyl-3-[3-(3,5-di-t-butyl-4-hydroxyphenyl)-1-oxopropyl]pyrrole.

3D. Formula X Where R is Other Than Methyl, m is 1–3 and n is 0–1

Similarly, by following the procedure of part A above and substituting for 3-(3,5-di-t-butyl-4-hydroxybenzoyl)pyrrole the following starting materials:
3-(3,5-di-t-butyl-4-hydroxybenzyl)pyrrole, and
3-[2-(3,5-di-t-butyl-4-hydroxyphenyl)-1-oxoethyl]pyrrole,
and substituting for methyl iodide the following starting materials:
ethyl iodide, and
benzyl bromide;
there are obtained the following compounds:
N-ethyl-3-(3,5-di-t-butyl-4-hydroxybenzyl)pyrrole,
N-benzyl-3-(3,5-di-t-butyl-4-hydroxybenzyl)pyrrole,
N-ethyl-3-[2-(3,5-di-t-butyl-4-hydroxyphenyl)-1-oxoethyl]pyrrole, and
N-benzyl-3-[2-(3,5-di-t-butyl-4-hydroxyphenyl)-1-oxoethyl]pyrrole.

3E. Formula X Where R is Methyl and X, Y and/or Z is Lower Alkyl or Halo

Similarly, by following the procedure of part A above and substituting for 3-(3,5-di-t-butyl-4-hydroxybenzoyl)pyrrole the following starting materials:
2,5-dimethyl-3-(3,5-di-t-butyl-4-hydroxybenzoyl)pyrrole,
3-ethyl-4-(3,5-di-t-butyl-4-hydroxybenzoyl)pyrrole,
2-(trifluoromethyl)-4-(3,5-di-t-butyl-4-hydroxybenzoyl)pyrrole, and
2-chloro-4-(3,5-di-t-butyl-4-hydroxybenzoyl)pyrrole;
there are obtained the following compounds:
N-methyl-2,5-dimethyl-3-(3,5-di-t-butyl-4-hydroxybenzoyl)pyrrole,
N-methyl-3-ethyl-4-(3,5-di-t-butyl-4-hydroxybenzoyl)pyrrole,
N-methyl-2-(trifluoromethyl)-4-(3,5-di-t-butyl-4-hydroxybenzoyl)pyrrole, and
N-methyl-2-chloro-4-(3,5-di-t-butyl-4-hydroxybenzoyl)pyrrole.

EXAMPLE 4

Synthesis of N-ethyl-3-(3,5-di-t-butyl-4-hydroxybenzoyl)pyrrole

4A. Formula X Where R is Ethyl

2 G (6.6 mmol) of 3-(3,5-di-t-butyl-4-hydroxybenzoyl)pyrrole were added to a cooled, stirred suspension of 0.70 g of sodium hydride (50% in mineral oil) in 50 ml of anhydrous dimethylformamide under nitrogen. After 30 minutes at room temperature, 0.7 ml of ethyl iodide was added, and stirring at room temperature was continued for an additional 2 hours. The reaction mixture was poured over a 10% HCl-ice mixture, then extracted three times with 250 ml ethyl acetate. The organic layer was washed five times with 200 ml water, dried and evaporated to dryness. The residue was purified by chromatography on alumina (3% water, 100 g) eluting with hexane:ethyl acetate (9:1). Crystallization from methylene chloride-hexane gave 1.11 g of N-ethyl-3-(3,5-di-t-butyl-4-hydroxybenzoyl)pyrrole (mp 73°–75° C.).

$^1$H nmr: 1.5m (21H), 3.93c (2H), 5.56s (OH), 6.63m (2H), 7.25m (1H), 7.80s (2H).

Anal. Calcd. for $C_{21}H_{29}NO_2$ (mw 333.94): Theoretical: C, 75.52; H, 8.90; N, 4.19. Found: C, 75.83; H, 8.95; N, 4.12.

4B. Formula X Where R is Propyl

Similarly, by following the procedure of part A above and substituting propyl iodide for ethyl iodide, there is obtained N-propyl-3-(3,5-di-t-butyl-4-hydroxybenzoyl)pyrrole.

EXAMPLE 5

Synthesis of N-n-butyl-3-(3,5-di-t-butyl-4-hydroxybenzoyl)pyrrole

5A. Formula X Where R is n-Butyl

2 G (6.6 mmol) of 3-(3,5-di-t-butyl-4-hydroxybenzoyl)pyrrole were added to a cooled, stirred suspension of 0.69 g of sodium hydride (50% in mineral oil) in 50 ml of anhydrous dimethylformamide under nitrogen. After 1 hour at 20° C., 0.8 ml of n-butyl bromide was added. Stirring was continued for an additional 18 hours at room temperature. The reaction mixture was poured over a 10% HCl-ice mixture, then extracted three times with 250 ml ethyl acetate. The organic layer was washed five times with 200 ml water, dried and evaporated to dryness. The residue was purified on a silica column (200 g) eluting with hexane:ethyl acetate (9:1). Crystallization from acetone-hexane gave 1.52 g of N-n-butyl-3-(3,5-di-t-butyl-4-hydroxybenzoyl)pyrrole (mp 101°–103° C.).

$^1$H nmr: 0.9t (3H), 1.5s (18H), 1.63m (4H), 3.9t (2H), 5.6s (OH), 6.68d (1H), 7.26m (1H), 7.86s (2H).

Anal. Calcd. for $C_{23}H_{33}ON$ (mw 355.49): Theoretical: C, 77.70; H, 9.35; N, 3.94. Found: C, 77.55; H, 9.52; N, 3.80.

5B. Formula X Where R is Lower Alkyl Other Than n-Butyl

Similarly, by following the procedure of part A above and substituting for n-butyl bromide the following starting materials:
s-butyl bromide, and
i-propyl bromide;
there are obtained the following respective compounds:
N-s-butyl-3-(3,5-di-t-butyl-4-hydroxybenzoyl)pyrrole, and
N-i-propyl-3-(3,5-di-t-butyl-4-hydroxybenzoyl)pyrrole.

EXAMPLE 6

Synthesis of N-benzyl-3-(3,5-di-t-butyl-4-hydroxybenzoyl)pyrrole

6A. Formula X Where R is Benzyl

2 G (6.6 mmol) of 3-(3,5-di-t-butyl-4-hydroxybenzoyl)pyrrole were added to a cooled, stirred suspension of 0.70 g of sodium hydride (50% in mineral oil) in 50 ml of anhydrous dimethylformamide under nitrogen. After 30 minutes at room temperature, 1.0 ml of benzyl bromide was added. Stirring at room temperature was continued for an additional 16 hours. The reaction mixture was poured over a 10% HCl-ice mixture, then extracted three times with 250 ml ethyl acetate. The organic layer was washed five times with 200 ml water, dried and evaporated to dryness. The residue was purified by chromatography on alumina (3% water, 100 g) eluting with hexane:ethyl acetate (9:1). Crystallization from methylene chloride-hexane gave 1.5 g of N-benzyl-3-(3,5-di-t-butyl-4-hydroxybenzoyl)pyrrole (mp 123°–124° C.).

$^1$H nmr: 1.45s (18H), 5.06s (2H), 5.56s (OH), 6.73m (2H), 7.31m (6H), 7.76s (2H).

Anal. Calcd. for $C_{26}H_{31}O_2N$ (mw 389.51): Theoretical: C, 80.16; H, 8.02; N, 3.59. Found: C, 80.17; H, 8.17; N, 3.47.

EXAMPLE 7

Synthesis of N-methyl-2,4,5-trichloro-3-(3,5-di-t-butyl-4-hydroxybenzoyl)pyrrole 7A. Formula X Where R is Methyl and X, Y and Z are Cl 2,4,5-Trichloro-3-(3,5-di-t-butyl-4-hydroxybenzoyl)pyrrole (3.3 g) dissolved in DMF (35 ml) was treated with sodium hydride (50%, 0.432 g) in 4 portions, under nitrogen with stirring at room temperature. After 1 hour at room temperature, 0.56 ml of methyl iodide was added, dropwise, via microsyringe. After stirring 5 minutes more, the reaction mixture was poured into water (300 ml). The organic layer was separated, dried and evaporated to dryness. The residue was purified on silica gel, eluting with hexane:ethyl acetate (80:20). The pure product was recrystallized from ether-pentane to give 2.73 g of the title compound (mp 155°–156° C.).

7B. Formula X Where R is Other Than Methyl

Similarly, by following the procedure of part A above and substituting for methyl iodide the following starting materials:
bromoacetic acid (with an additional molar equivalent of NaH),
benzyl bromide,
s-butyl bromide, and
n-propyl bromide;
there are obtained the following respective compounds:
2,4,5-trichloro-3-(3,5-di-t-butyl-4-hydroxybenzoyl)pyrrole-N-acetic acid,
N-benzyl-2,4,5-trichloro-3-(3,5-di-t-butyl-4-hydroxybenzoyl)pyrrole,
N-s-butyl-2,4,5-trichloro-3-(3,5-di-t-butyl-4-hydroxybenzoyl)pyrrole, and
N-n-propyl-2,4,5-trichloro-3-(3,5-di-t-butyl-4-hydroxybenzoyl)pyrrole.

7C. Formula X Where X, Y and/or Z is Halo Other Than Trichloro

Similarly, by following the procedure of part A above and substituting for 2,4,5-trichloro-3-(3,5-di-t-butyl-4-hydroxybenzoyl)pyrrole the following starting materials:
2,5-dichloro-3-(3,5-di-t-butyl-4-hydroxybenzoyl)pyrrole,
2,4,5-tribromo-3-(3,5-di-t-butyl-4-hydroxybenzoyl)pyrrole, and
2-chloro-4-(3,5-di-t-butyl-4-hydroxybenzoyl)pyrrole;
there are obtained the following respective compounds:
N-methyl-2,5-dichloro-3-(3,5-di-t-butyl-4-hydroxybenzoyl)pyrrole,
N-methyl-2,4,5-tribromo-3-(3,5-di-t-butyl-4-hydroxybenzoyl)pyrrole, and
N-methyl-2-chloro-4-(3,5-di-t-butyl-4-hydroxybenzoyl)pyrrole.

7D. Formula X Where R is Other Than Methyl and X is Halo Other Than Trichloro

Similarly, by following the procedure of part C above and substituting for methyl iodide the following starting materials:
benzyl bromide,
s-butyl bromide, and
n-propyl bromide;
there are obtained the following respective compounds:
N-benzyl-2,5-dichloro-3-(3,5-di-t-butyl-4-hydroxybenzoyl)pyrrole,
N-benzyl-2,4,5-tribromo-3-(3,5-di-t-butyl-4-hydroxybenzoyl)pyrrole,
N-benzyl-2-chloro-4-(3,5-di-t-butyl-4-hydroxybenzoyl)pyrrole,
N-s-butyl-2,5-dichloro-3-(3,5-di-t-butyl-4-hydroxybenzoyl)pyrrole,
N-s-butyl-2,4,5-tribromo-3-(3,5-di-t-butyl-4-hydroxybenzoyl)pyrrole,
N-s-butyl-2-chloro-4-(3,5-di-t-butyl-4-hydroxybenzoyl)pyrrole,
N-n-propyl-2,5-dichloro-3-(3,5-di-t-butyl-4-hydroxybenzoyl)pyrrole,
N-n-propyl-2,4,5-tribromo-3-(3,5-di-t-butyl-4-hydroxybenzoyl)pyrrole, and
N-n-propyl-2-chloro-4-(3,5-di-t-butyl-4-hydroxybenzoyl)pyrrole.

7E. Formula X Where m is 1 and n is 0

Similarly, by following the procedure of part A above and substituting 2,4,5-trichloro-3-(3,5-di-t-butyl-4-hydroxybenzyl)pyrrole for 2,4,5-trichloro-3-(3,5-di-t-butyl-4-hydroxybenzoyl)pyrrole, there is obtained N-methyl-2,4,5-trichloro-3-(3,5-di-t-butyl-4-hydroxybenzyl)pyrrole.

EXAMPLE 8

Synthesis of N-methyl-2-methylthio-4-(3,5-di-t-butyl-4-hydroxybenzoyl)pyrrole

8A. Formula X Where R is Methyl and X is SR'

2-Methylthio-4-(3,5-di-t-butyl-4-hydroxybenzoyl)pyrrole (1 g) was added to a cooled, stirred suspension of 0.28 g of sodium hydride (50% in mineral oil) in 20 ml of anhydrous dimethylformamide under nitrogen. After 45 minutes at room temperature, the mixture was cooled to 0° C. and 0.25 ml of methyl iodide was added. After 30 minutes, the reaction mixture was poured into a 10% HCl-ice-water mixture, then extracted three times with 100 ml ethyl acetate. The organic layer was washed five times with 100 ml water, dried and evaporated to dryness. Crystallization of the residue from ethyl acetate-hexane gave 0.93 g of the title compound (mp 173°–175° C.).

8B. Formula X Where R is Other Than Methyl

Similarly, by following the procedure of part A above and substituting for methyl iodide the following starting materials:
bromoacetic acid (with an additional molar equivalent of NaH),
benzyl bromide,
s-butyl bromide, and
n-propyl bromide;
there are obtained the following respective compounds:
2-methylthio-4-(3,5-di-t-butyl-4-hydroxybenzoyl)pyrrole-N-acetic acid,
N-benzyl-2-methylthio-4-(3,5-di-t-butyl-4-hydroxybenzoyl)pyrrole,
N-s-butyl-2-methylthio-4-(3,5-di-t-butyl-4-hydroxybenzoyl)pyrrole, and
N-n-propyl-2-methylthio-4-(3,5-di-t-butyl-4-hydroxybenzoyl)pyrrole.

8C. Formula X Where X is a Sulfur-based Radical Other Than 2-Methylthio

Similarly, by following the procedure of part A above and substituting for 2-methylthio-4-(3,5-di-t-butyl-4-hydroxybenzoyl)pyrrole the following starting materials:

3-methylthio-4-(3,5-di-t-butyl-4-hydroxybenzoyl)pyrrole,
2,3-dimethylthio-4-(3,5-di-t-butyl-4-hydroxybenzoyl)pyrrole,
2-ethylthio-4-(3,5-di-t-butyl-4-hydroxybenzoyl)pyrrole,
3-(3,5-di-t-butyl-4-hydroxybenzoyl)-5-thiocyanopyrrole,
2,3-dithiocyano-4-(3,5-di-t-butyl-4-hydroxybenzoyl)pyrrole,
2-methylsulfinyl-4-(3,5-di-t-butyl-4-hydroxybenzoyl)pyrrole,
2,5-dimethylsulfinyl-3-(3,5-di-t-butyl-4-hydroxybenzoyl)pyrrole, and
3-methylsulfonyl-4-(3,5-di-t-butyl-4-hydroxybenzoyl)pyrrole;
there are obtained the following respective compounds:
N-methyl-3-methylthio-4-(3,5-di-t-butyl-4-hydroxybenzoyl)pyrrole,
N-methyl-2,3-dimethylthio-4-(3,5-di-t-butyl-4-hydroxybenzoyl)pyrrole,
N-methyl-2-ethylthio-4-(3,5-di-t-butyl-4-hydroxybenzoyl)pyrrole,
N-methyl-3-(3,5-di-t-butyl-4-hydroxybenzoyl)-5-thiocyanopyrrole,
N-methyl-2,3-dithiocyano-4-(3,5-di-t-butyl-4-hydroxybenzoyl)pyrrole,
N-methyl-2-methylsulfinyl-4-(3,5-di-t-butyl-4-hydroxybenzoyl)pyrrole,
N-methyl-2,5-dimethylsulfinyl-3-(3,5-di-t-butyl-4-hydroxybenzoyl)pyrrole, and
N-methyl-3-methylsulfonyl-4-(3,5-di-t-butyl-4-hydroxybenzoyl)pyrrole.

8D. Formula X Where X is a Sulfur-based Radical Other Than 2-Methylthio and R is Other Than Methyl Similarly, by following the procedure of part A above and substituting for 2-methylthio-4-(3,5-di-t-butyl-4-hydroxybenzoyl)pyrrole the following starting materials:
2-ethylthio-4-(3,5-di-t-butyl-4-hydroxybenzoyl)pyrrole,
3-thiocyano-4-[2-(3,5-di-t-butyl-4-hydroxybenzoyl)-1-oxoethyl]pyrrole, and
2-methylsulfinyl-4-(3,5-di-t-butyl-4-hydroxybenzoyl)pyrrole,
and substituting for methyl iodide the following starting materials:
ethyl iodide, and
benzyl bromide;
there may be obtained the following compounds:
N-ethyl-2-ethylthio-4-(3,5-di-t-butyl-4-hydroxybenzoyl)pyrrole,
N-ethyl-3-[2-(3,5-di-t-butyl-4-hydroxybenzoyl)-1-oxoethyl]-4-thiocyanopyrrole,
N-ethyl-2-methylsulfinyl-4-(3,5-di-t-butyl-4-hydroxybenzoyl)pyrrole,
N-benzyl-2-ethylthio-4-(3,5-di-t-butyl-4-hydroxybenzoyl)pyrrole,
N-benzyl-3-[2-(3,5-di-t-butyl-4-hydroxybenzoyl)-1-oxoethyl]-4-thiocyanopyrrole, and
N-benzyl-2-methylsulfinyl-4-(3,5-di-t-butyl-4-hydroxybenzoyl)pyrrole.

8E. Formula X Where m is 1–3 and n is 0–1

Similarly, by following the procedure of part A above and substituting for 2-methylthio-4-(3,5-di-t-butyl-4-hydroxybenzoyl)pyrrole the following starting materials:
2-methylthio-4-(3,5-di-t-butyl-4-hydroxybenzyl)pyrrole, and
2-methylthio-4-[2-(3,5-di-t-butyl-4-hydroxyphenyl)-1-oxoethyl]pyrrole,
there may be obtained the following compounds:
N-methyl-2-methylthio-4-(3,5-di-t-butyl-4-hydroxybenzyl)pyrrole, and
N-methyl-2-methylthio-4-[2-(3,5-di-t-butyl-4-hydroxyphenyl)-1-oxoethyl]pyrrole.

EXAMPLE 9

Synthesis of
2-chloro-4-(3,5-di-t-butyl-4-hydroxybenzoyl)pyrrole
and
2,3-di-chloro-4-(3,5-di-t-butyl-4-hydroxybenzoyl)pyrrole 9A. Formula X Where X and/or Y is Cl A stirred solution of 2 g (6.68 mmol) of 3-(3,5-di-t-butyl-4-hydroxybenzoyl)pyrrole in 25 ml of anhydrous methylene chloride was treated dropwise, at room temperature, with 0.26 ml (450 mg, 3.34 mmol) of sulfuryl chloride. The resulting mixture was stirred for 30 minutes and then poured into saturated sodium bicarbonate solution. The organic phase was separated and the aqueous phase extracted with methylene chloride. The combined organic extract was dried and evaporated under vacuo. The residue was purified by repeated tlc, using hexane-ethyl acetate (80:20) for the first development, thus obtaining 413 mg of recovered starting material plus 1.144 g of a mixture of more polar products.

This mixture was separated by tlc using methylene chloride (2 developments), and recrystallized from ethyl acetate-hexane, to afford:

(a) 462 mg (20.7%) of 2-chloro-4-(3,5-di-t-butyl-4-hydroxybenzoyl)pyrrole, a compound according to Formula X wherein: m is 0; n is 1; R is H; X is Cl; and Y and Z are both H (mp 222°–223° C.);

Anal. Calcd. for $C_{19}H_{24}ClNO_2$ (mw 333.84): Theoretical: C, 68.35; H, 7.24; N, 4.19. Found: C, 68.60; H, 7.14; N, 4.13.

and (b) 604 mg (24.5%) of 2,3-dichloro-4-(3,5-di-t-butyl-4-hydroxybenzoyl)pyrrole, a compound according to Formula X wherein: m is 0; n is 1; R is H; X and Y are each Cl; and Z is H (mp 258°–259° C.—uncorrected);

Anal. Calcd. for $C_{19}H_{23}Cl_2NO_2$ (mw 368.287): Theoretical: C, 61.95; H, 6.29; N, 3.80. Found: C, 61.97; H, 6.21; N, 3.70.

9B. Formula X Where X and/or Y is Cl and R is Lower Alkyl or Benzyl

Similarly, by following the procedure of part A above and substituting for 3-(3,5-di-t-butyl-4-hydroxybenzoyl)pyrrole the following starting materials:
N-methyl-3-(3,5-di-t-butyl-4-hydroxybenzoyl)pyrrole,
N-ethyl-3-(3,5-di-t-butyl-4-hydroxybenzoyl)pyrrole,
N-i-propyl-3-(3,5-di-t-butyl-4-hydroxybenzoyl)pyrrole,
N-butyl-3-(3,5-di-t-butyl-4-hydroxybenzoyl)pyrrole, and
N-benzyl-3-(3,5-di-t-butyl-4-hydroxybenzoyl)pyrrole,
there are obtained the following respective compounds:
N-methyl-2-chloro-4-(3,5-di-t-butyl-4-hydroxybenzoyl)pyrrole,
N-methyl-2,3-dichloro-4-(3,5-di-t-butyl-4-hydroxybenzoyl)pyrrole,
N-ethyl-2-chloro-4-(3,5-di-t-butyl-4-hydroxybenzoyl)pyrrole,
N-ethyl-2,3-dichloro-4-(3,5-di-t-butyl-4-hydroxybenzoyl)pyrrole, N-i-propyl-2-chloro-4-(3,5-di-t-butyl-4-hydroxybenzoyl)pyrrole,
N-i-propyl-2,3-dichloro-4-(3,5-di-t-butyl-4-hydroxybenzoyl)pyrrole,
N-butyl-2-chloro-4-(3,5-di-t-butyl-4-hydroxybenzoyl)pyrrole,
N-butyl-2,3-dichloro-4-(3,5-di-t-butyl-4-hydroxybenzoyl)pyrrole,
N-benzyl-2-chloro-4-(3,5-di-t-butyl-4-hydroxybenzoyl)pyrrole, and
N-benzyl-2,3-dichloro-4-(3,5-di-t-butyl-4-hydroxybenzoyl)pyrrole.

9C. Formula X Where X and/or Y is Cl, m is 1–3 and n is 0–1

Similarly, by following the procedure of part A above and substituting for 3-(3,5-di-t-butyl-4-hydroxybenzoyl)pyrrole the following starting materials:
3-(3,5-di-t-butyl-4-hydroxybenzyl)pyrrole,
3-[3-(3,5-di-t-butyl-4-hydroxyphenyl)propyl]pyrrole,
3-[2-(3,5-di-t-butyl-4-hydroxyphenyl)-1-oxoethyl]pyrrole, and
3-[3-(3,5-di-t-butyl-4-hydroxyphenyl)-1-oxopropyl]pyrrole,
there may be obtained the following respective compounds:
2-chloro-4-(3,5-di-t-butyl-4-hydroxybenzyl)pyrrole,
2,3-dichloro-4-(3,5-di-t-butyl-4-hydroxybenzyl)pyrrole,
2-chloro-4-[3-(3,5-di-t-butyl-4-hydroxyphenyl)propyl]pyrrole,
2,3-dichloro-4-[3-(3,5-di-t-butyl-4-hydroxyphenyl)propyl]pyrrole,
2-chloro-4-[2-(3,5-di-t-butyl-4-hydroxyphenyl)-1-oxoethyl]pyrrole,
2,3-dichloro-4-[2-(3,5-di-t-butyl-4-hydroxyphenyl)-1-oxoethyl]pyrrole
2-chloro-4-[3-(3,5-di-t-butyl-4-hydroxyphenyl)-1-oxopropyl]pyrrole, and
2,3-dichloro-4-[3-(3,5-di-t-butyl-4-hydroxyphenyl)-1-oxopropyl]pyrrole.

9D. Formula X Where X and/or Y is Cl, R is Other Than Methyl, m is 1–3 and n is 0–1

Similarly, by following the procedure of part A above and substituting for 3-(3,5-di-t-butyl-4-hydroxybenzoyl)pyrrole the following starting materials:
N-benzyl-3-(3,5-di-t-butyl-4-hydroxybenzyl)pyrrole, and
N-ethyl-3-[2-(3,5-di-t-butyl-4-hydroxyphenyl)-1-oxoethyl]pyrrole;
there may be obtained the following compounds:
N-benzyl-2-chloro-4-(3,5-di-t-butyl-4-hydroxybenzyl)pyrrole,
N-benzyl-2,3-dichloro-4-(3,5-di-t-butyl-4-hydroxybenzyl)pyrrole,
N-ethyl-2-chloro-4-[2-(3,5-di-t-butyl-4-hydroxyphenyl)-1-oxoethyl]pyrrole, and
N-ethyl-2,3-dichloro-4-[2-(3,5-di-t-butyl-4-hydroxyphenyl)-1-oxoethyl]pyrrole.

EXAMPLE 10

Synthesis of 2,5-dichloro-3-(3,5-di-t-butyl-4-hydroxybenzoyl)pyrrole and 2,4,5-trichloro-3-(3,5-di-t-butyl-4-hydroxybenzoyl)pyrrole 10A. Formula X Where X and Z, or X, Y and Z are Chloro A solution of 4 g. (13.3 mmol) of 3(3,5-di-t-butyl-4-hydroxybenzoyl)pyrrole in 30 ml of anhydrous methylene chloride was treated dropwise at room temperature and under stirring with 1.8 g (1.068 ml, 13.3 mmoles) of sulfuryl chloride. After 30 minutes, 1.068 ml more of this reagent was added. The mixture was stirred for 30 minutes further, and thereafter poured into saturated sodium bicarbonate solution. The organic layer was separated and the aqueous layer extracted with methylene chloride. The combined extracts were dried and the solvent eliminated under reduced pressure. The residue was purified by a combination of t.l.c. (silica gel) and column chromatography (deactivated alumina, 3% water) to afford:

711 mg (14.5%) of 2,5-dichloro-3-(3,5-di-t-butyl-4-hydroxybenzoyl)pyrrole, a compound according to Formula X wherein: m is 0; n is 1; R is H; Y is H; and X and Z are both Cl (mp 202°–203° C.).

Analysis calculated for $C_{19}H_{23}Cl_2NO_2$ (mw 368.287): Theoretical: C, 61.95; H, 6.29; N, 3.80. Found: C, 62.19; H, 6.07; N, 3.78.
and 990 mg (18.5%) of 2,4,5-trichloro-3-(3,5-di-t-butyl-4-hydroxybenzoyl)pyrrole, a compound according to Formula X wherein: m is 0; n is 1; R is H; and X, Y and Z are each Cl (mp 212°–213° C.).

Analysis calculated for $C_{19}H_{22}Cl_3NO_2$ (mw 402.747): Theoretical: C, 56.65; H, 5.50; N, 3.47. Found: C, 56.65; H, 5.49; N, 3.43.

10B. Formula X Where X and Z, or X, Y and Z are Chloro and R is Lower Alkyl or Benzyl Similarly, by following the procedure of part A above and substituting for 3-(3,5-di-t-butyl-4-hydroxybenzoyl)pyrrole the following starting materials:
N-methyl-3-(3,5-di-t-butyl-4-hydroxybenzoyl)pyrrole,
N-ethyl-3-(3,5-di-t-butyl-4-hydroxybenzoyl)pyrrole,
N-i-propyl-3-(3,5-di-t-butyl-4-hydroxybenzoyl)pyrrole,
N-butyl-3-(3,5-di-t-butyl-4-hydroxybenzoyl)pyrrole, and
N-benzyl-3-(3,5-di-t-butyl-4-hydroxybenzoyl)pyrrole,
there are obtained the following respective compounds:
N-methyl-2,5-dichloro-4-(3,5-di-t-butyl-4-hydroxybenzoyl)pyrrole,
N-methyl-2,4,5-trichloro-3-(3,5-di-t-butyl-4-hydroxybenzoyl)pyrrole,
N-ethyl-2,5-dichloro-4-(3,5-di-t-butyl-4-hydroxybenzoyl)pyrrole,
N-ethyl-2,4,5-trichloro-3-(3,5-di-t-butyl-4-hydroxybenzoyl)pyrrole,
N-i-propyl-2,5-dichloro-4-(3,5-di-t-butyl-4-hydroxybenzoyl)pyrrole,
N-i-propyl-2,4,5-trichloro-3-(3,5-di-t-butyl-4-hydroxybenzoyl)pyrrole,
N-butyl-2,5-dichloro-4-(3,5-di-t-butyl-4-hydroxybenzoyl)pyrrole,
N-butyl-2,4,5-trichloro-3-(3,5-di-t-butyl-4-hydroxybenzoyl)pyrrole,
N-benzyl-2,5-dichloro-4-(3,5-di-t-butyl-4-hydroxybenzoyl)pyrrole, and
N-benzyl-2,4,5-trichloro-3-(3,5-di-t-butyl-4-hydroxybenzoyl)pyrrole.

10C. Formula X Where X and Z, or X, Y and Z are Chloro, m is 1–3 and n is 0–1

Similarly, by following the procedure of part A above and substituting for 3-(3,5-di-t-butyl-4-hydroxybenzoyl)pyrrole the following starting materials:
3-(3,5-di-t-butyl-4-hydroxybenzyl)pyrrole,
3-[3-(3,5-di-t-butyl-4-hydroxyphenyl)propyl]pyrrole, 3-[2-(3,5-di-t-butyl-4-hydroxyphenyl)-1-oxoethyl]pyrrole, and
3-[3-(3,5-di-t-butyl-4-hydroxyphenyl)-1-oxopropyl]pyrrole,
there may be obtained the following respective compounds:
2,5-dichloro-4-(3,5-di-t-butyl-4-hydroxybenzyl)pyrrole,
2,4,5-trichloro-3-(3,5-di-t-butyl-4-hydroxybenzyl)pyrrole,
2,5-dichloro-4-[3-(3,5-di-t-butyl-4-hydroxyphenyl)propyl]pyrrole,
2,4,5-trichloro-3-[3-(3,5-di-t-butyl-4-hydroxyphenyl)propyl]pyrrole,
2,5-dichloro-4-[2-(3,5-di-t-butyl-4-hydroxyphenyl)-1-oxoethyl]pyrrole,
2,4,5-trichloro-3-[2-(3,5-di-t-butyl-4-hydroxyphenyl)-1-oxoethyl]pyrrole,
2,5-dichloro-4-[3-(3,5-di-t-butyl-4-hydroxyphenyl)-1-oxopropyl]pyrrole, and
2,4,5-trichloro-3-[3-(3,5-di-t-butyl-4-hydroxyphenyl)-1-oxopropyl]pyrrole.

10D. Formula X Where X and Z, or X, Y and Z are Chloro, R is Other Than Methyl, m is 1-3 and n is 0-1

Similarly, by following the procedure of part A above and substituting for 3-(3,5-di-t-butyl-4-hydroxybenzoyl)pyrrole the following starting materials:
N-benzyl-3-(3,5-di-t-butyl-4-hydroxybenzyl)pyrrole, and
N-ethyl-3-[2-(3,5-di-t-butyl-4-hydroxyphenyl)-1-oxoethyl]pyrrole;
there may be obtained the following compounds:
N-benzyl-2,5-dichloro-4-(3,5-di-t-butyl-4-hydroxybenzyl)pyrrole,
N-benzyl-2,4,5-trichloro-3-(3,5-di-t-butyl-4-hydroxybenzyl)pyrrole,
N-ethyl-2,5-dichloro-4-[2-(3,5-di-t-butyl-4-hydroxyphenyl)-1-oxoethyl]pyrrole, and
N-ethyl-2,4,5-trichloro-3-[2-(3,5-di-t-butyl-4-hydroxyphenyl)-1-oxoethyl]pyrrole.

EXAMPLE 11

Synthesis of 2-chloro-4-(3,5-di-t-butyl-4-hydroxybenzoyl)pyrrole

11A. Formula X Where X is Chloro 1.0 G (0.003 mole) of 3-(3,5-di-t-butyl-4-hydroxybenzoyl)pyrrole was dissolved in 40 ml of methylene chloride and 10 ml of acetone, and cooled to 0° C. The cooled solution was stirred and to it was added 0.585 g (0.0029 mole) of 1,3-dichloro-5,5-dimethylhydantoin. Stirring was continued for 90 minutes at 0° C. The reaction mixture was washed with water. The organic phase was dried over sodium sulfate and the solvent was removed in vacuo. The residue was purified by t.l.c. (silica gel) using hexane:ethyl acetate (3:1) as the developing solvent, followed by recrystallization to yield 43% of the title compound, 2-chloro-4-(3,5-di-t-butyl-4-hydroxybenzoyl)pyrrole (having the same analytical characteristics for the compound as made in Example 9A).

11B. Formula X Where X is Cl and R is Lower Alkyl or Benzyl

Similarly, by following the procedure of part A above and substituting for 3-(3,5-di-t-butyl-4-hydroxybenzoyl)pyrrole the following starting materials:
N-methyl-3-(3,5-di-t-butyl-4-hydroxybenzoyl)pyrrole,
N-ethyl-3-(3,5-di-t-butyl-4-hydroxybenzoyl)pyrrole,
N-i-propyl-3-(3,5-di-t-butyl-4-hydroxybenzoyl)pyrrole,
N-butyl-3-(3,5-di-t-butyl-4-hydroxybenzoyl)pyrrole, and
N-benzyl-3-(3,5-di-t-butyl-4-hydroxybenzoyl)pyrrole,
there are obtained the following respective compounds:
N-methyl-2-chloro-4-(3,5-di-t-butyl-4-hydroxybenzoyl)pyrrole,
N-ethyl-2-chloro-4-(3,5-di-t-butyl-4-hydroxybenzoyl)pyrrole,
N-i-propyl-2-chloro-4-(3,5-di-t-butyl-4-hydroxybenzoyl)pyrrole,
N-butyl-2-chloro-4-(3,5-di-t-butyl-4-hydroxybenzoyl)pyrrole, and
N-benzyl-2-chloro-4-(3,5-di-t-butyl-4-hydroxybenzoyl)pyrrole.

11C. Formula X Where X is Cl, m is 1-3 and n is 0-1

Similarly, by following the procedure of part A above and substituting for 3-(3,5-di-t-butyl-4-hydroxybenzoyl)pyrrole the following starting materials:
3-(3,5-di-t-butyl-4-hydroxybenzyl)pyrrole,
3-[3-(3,5-di-t-butyl-4-hydroxyphenyl)propyl]pyrrole,
3-[2-(3,5-di-t-butyl-4-hydroxyphenyl)-1-oxoethyl]pyrrole, and
3-[3-(3,5-di-t-butyl-4-hydroxyphenyl)-1-oxopropyl]pyrrole,
there may be obtained the following respective compounds:
2-chloro-4-(3,5-di-t-butyl-4-hydroxybenzy)pyrrole,
2-chloro-4-[3-(3,5-di-t-butyl-4-hydroxyphenyl)propyl]pyrrole,
2-chloro-4-[2-(3,5-di-t-butyl-4-hydroxyphenyl)-1-oxoethyl]pyrrole, and
2-chloro-4-[3-(3,5-di-t-butyl-4-hydroxyphenyl)-1-oxopropyl]pyrrole.

11D. Formula X Where X is Cl, R is Other Than Methyl, m is 1-3 and n is 0-1

Similarly, by following the procedure of part A above and substituting for 3-(3,5-di-t-butyl-4-hydroxybenzoyl)pyrrole the following starting materials:
N-benzyl-3-(3,5-di-t-butyl-4-hydroxybenzyl)pyrrole, and
N-ethyl-3-[2-(3,5-di-t-butyl-4-hydroxyphenyl)-1-oxoethyl]pyrrole;
there may be obtained the following compounds:
N-benzyl-2-chloro-4-(3,5-di-t-butyl-4-hydroxybenzyl)pyrrole, and
N-ethyl-2-chloro-4-[2-(3,5-di-t-butyl-4-hydroxyphenyl)-1-oxoethyl]pyrrole.

EXAMPLE 12

Synthesis of 1,2,4,5-tetrachloro-3-(3,5-di-t-butyl-4-hydroxybenzoyl)pyrrole

12A. Formula X Where R, X, Y and Z are Chloro 50.0 G (0.167 mole) of 3-(3,5-di-t-butyl-4-hydroxybenzoyl)pyrrole was suspended in 500 ml of methylene chloride and cooled to −70° C. with stirring. To this was added, all at once, 60 ml (0.746 mole) of sulfuryl chloride. The cooling bath was removed and the reaction temperature slowly rose to 20° C. (room temperature). Stirring was continued for 20 hours. The reaction mixture was poured onto ice/water and the product was extracted with methylene chloride. The extract was washed with water, dried over sodium sulfate, and evaporated in vacuo to a volume of about 1 liter. The solution was filtered through a short column of Silica gel (1 kg). The desired product, 1,2,4,5-tetrachloro-3-(3,5-di-t-butyl-4-hydroxybenzoyl)pyrrole, was removed from the column with methylene chloride. Chrystallization from acetone-hexane yielded 38.8 g (53%) of the title compound [mp 106°–108° C.; $^1$H nmr: 1.45s (18H), 6.00s (OH), 7.75s (2H)].

12B. Formula X Where X, Y and Z are Chloro, m is 1–3 and n is 0–1

Similarly, by following the procedure of part A above and substituting for 3-(3,5-di-t-butyl-4-hydroxybenzoyl)pyrrole the following starting materials:
3-(3,5-di-t-butyl-4-hydroxybenzyl)pyrrole,
3-[3-(3,5-di-t-butyl-4-hydroxyphenyl)propyl]pyrrole,
3-[2-(3,5-di-t-butyl-4-hydroxyphenyl)-1-oxoethyl]pyrrole, and
3-[3-(3,5-di-t-butyl-4-hydroxyphenyl)-1-oxopropyl]pyrrole,
there may be obtained the following respective compounds:
1,2,4,5-tetrachloro-3-(3,5-di-t-butyl-4-hydroxybenzyl)pyrrole,
1,2,4,5-tetrachloro-3-[3-(3,5-di-t-butyl-4-hydroxyphenyl)propyl]pyrrole,
1,2,4,5-tetrachloro-3-[2-(3,5-di-t-butyl-4-hydroxyphenyl)-1-oxoethyl]pyrrole, and
1,2,4,5-tetrachloro-3-[3-(3,5-di-t-butyl-4-hydroxyphenyl)-1-oxopropyl]pyrrole.

EXAMPLE 13

Synthesis of 2,4,5-trichloro-3-(3,5-di-t-butyl-4-hydroxybenzoyl)pyrrole

13A. Formula X Where X, Y and Z are Chloro 38.8 G (0.088 mole) of 1,2,4,5-tetrachloro-3-(3,5-di-t-butyl-4-hydroxybenzoyl)pyrrole, as prepared in Example 12A, was suspended in 250 ml of acetone and 250 ml of acetic acid:water (4:1) and stirred. To the stirred mixture at room temperature 15.23 g (0.091 mole) of potassium iodide was added in a 10 minute period, and thereafter 11.5 g (0.091 mole) of sodium sulfite and 500 ml of water were aadded. Agitation was continued for 30 minutes. The precipitated solid was collected by filtration and washed with water. This solid was dissolved in ethyl acetate, dried over sodium sulfite, and evaporated in vacuo. The residue was recrystallized from petroleum ether to give 29.9 g (45% yield based on the starting material of Example 12A) of the title material, 2,4,5-trichloro-3-(3,5-di-t-butyl-4-hydroxybenzoyl)pyrrole, having physical constants identical to those obtained by the procedure of Example 10A.

13B. Formula X Where X, Y and Z are Chloro, m is 1–3 and n is 0–1

Similarly, by following the procedure of part A above and substituting for 1,2,4,5-tetrachloro-3-(3,5-di-t-butyl-4-hydroxybenzoyl)pyrrole the following starting materials:
1,2,4,5-tetrachloro-3-(3,5-di-t-butyl-4-hydroxybenzyl)pyrrole,
1,2,4,5-tetrachloro-3-[3-(3,5-di-t-butyl-4-hydroxyphenyl)propyl]pyrrole,
1,2,4,5-tetrachloro-3-[2-(3,5-di-t-butyl-4-hydroxyphenyl)-1-oxoethyl]pyrrole, and
1,2,4,5-tetrachloro-3-[3-(3,5-di-t-butyl-4-hydroxyphenyl)-1-oxopropyl]pyrrole;
there may be obtained the following respective compounds:
2,4,5-trichloro-3-(3,5-di-t-butyl-4-hydroxybenzyl)pyrrole,
2,4,5-trichloro-3-[3-(3,5-di-t-butyl-4-hydroxyphenyl)propyl]pyrrole,
2,4,5-trichloro-3-[2-(3,5-di-t-butyl-4-hydroxyphenyl)-1-oxoethyl]pyrrole, and
2,4,5-trichloro-3-[3-(3,5-di-t-butyl-4-hydroxyphenyl)-1-oxopropyl]pyrrole.

EXAMPLE 14

Synthesis of 2-bromo-4-(3,5-di-t-butyl-4-hydroxybenzoyl)pyrrole

14A. Formula X Where X is Br

A cold ($-70°$ C.) solution of 2 g (6.6 mmol) of 3-(3,5-di-t-butyl-4-hydroxybenzoyl)pyrrole in 50 ml of anhydrous methylene chloride was treated dropwise, with stirring, with 1.067 (6.6 mmol) of bromine in 35 ml of methylene chloride. When the addition was complete, the reaction mixture was stirred for an additional hour. The solution was then poured into saturated sodium bicarbonate solution, the organic phase was separated and the aqueous phase extracted twice with methylene chloride. The combined extracts were dried and evaporated to dryness in vacuo.

Purification of the residue by t.l.c. using hexane-ethyl acetate (80:20) as eluant, afforded 774 mg (40.5%) of the title compound, a compound according to Formula X wherein: m is 0; n is 1; R is H; X is Br; and Y and Z are both H, which was recrystallized from hexane-ethyl acetate (mp 200°–201° C.).

Anal. Calcd. for $C_{19}H_{24}BrNO_2$ (mw 378.296): Theoretical: C, 60.32; H, 6.39; N, 3.70, Found: C, 60.17; H, 6.37; N, 3.61.

14B. Formula X Where X is Br and R is Lower Alkyl or Benzyl

Similarly, by following the procedure of part A above and substituting for 3-(3,5-di-t-butyl-4-hydroxybenzoyl)pyrrole the following starting materials:
N-methyl-3-(3,5-di-t-butyl-4-hydroxybenzoyl)pyrrole,
N-ethyl-3-(3,5-di-t-butyl-4-hydroxybenzoyl)pyrrole,
N-i-propyl-3-(3,5-di-t-butyl-4-hydroxybenzoyl)pyrrole,
N-butyl-3-(3,5-di-t-butyl-4-hydroxybenzoyl)pyrrole, and
N-benzyl-3-(3,5-di-t-butyl-4-hydroxybenzoyl)pyrrole,
there are obtained the following respective compounds:
N-methyl-2-bromo-4-(3,5-di-t-butyl-4-hydroxybenzoyl)pyrrole,
N-ethyl-2-bromo-4-(3,5-di-t-butyl-4-hydroxybenzoyl)pyrrole,
N-i-propyl-2-bromo-4-(3,5-di-t-butyl-4-hydroxybenzoyl)pyrrole,
N-butyl-2-bromo-4-(3,5-di-t-butyl-4-hydroxybenzoyl)pyrrole, and
N-benzyl-2-bromo-4-(3,5-di-t-butyl-4-hydroxybenzoyl)pyrrole.

14C. Formula X Where X is Br, m is 1–3 and n is 0–1

Similarly, by following the procedure of part A above and substituting for 3-(3,5-di-t-butyl-4-hydroxybenzoyl)pyrrole the following starting materials:
3-(3,5-di-t-butyl-4-hydroxybenzyl)pyrrole,
3-[3-(3,5-di-t-butyl-4-hydroxyphenyl)propyl]pyrrole,
3-[2-(3,5-di-t-butyl-4-hydroxyphenyl)-1-oxoethyl]pyrrole, and
3-[3-(3,5-di-t-butyl-4-hydroxyphenyl)-1-oxopropyl]pyrrole,
there may be obtained the following respective compounds:
2-bromo-4-(3,5-di-t-butyl-4-hydroxybenzyl)pyrrole, 2-bromo-4-[3-(3,5-di-t-butyl-4-hydroxyphenyl)propyl]-pyrrole,
2-bromo-4-[2-(3,5-di-t-butyl-4-hydroxyphenyl)-1-oxoethyl]pyrrole, and
2-bromo-4-[3-(3,5-di-t-butyl-4-hydroxyphenyl)-1-oxopropyl]pyrrole.

14D. Formula X Where X is Br, R is Other Than Methyl, m is 1–3 and n is 0–1

Similarly, by following the procedure of part A above and substituting for 3-(3,5-di-t-butyl-4-hydroxybenzoyl)pyrrole the following starting materials:
N-benzyl-3-(3,5-di-t-butyl-4-hydroxybenzyl)pyrrole, and
N-ethyl-3-[2-(3,5-di-t-butyl-4-hydroxyphenyl)-1-oxoethyl]pyrrole;
there may be obtained the following compounds:
N-benzyl-2-bromo-4-(3,5-di-t-butyl-4-hydroxybenzyl)pyrrole, and
N-ethyl-2-bromo-4-[2-(3,5-di-t-butyl-4-hydroxyphenyl)-1-oxoethyl]pyrrole.

14E. Formula X Where X is I

Similarly, by following the procedure of part A above and substituting elemental iodine for elemental bromine, there is obtained 2-iodo-4-(3,5-di-t-butyl-4-hydroxybenzoyl)pyrrole, for which the variations described in parts B–D are equally applicable.

EXAMPLE 15

Synthesis of 2,3-dibromo-4-(3,5-di-t-butyl-4-hydroxybenzoyl)pyrrole

15A. Formula X Where X and Y are Br

A solution of 2 g (6.6 mmol) of 3-(3,5-di-t-butyl-4-hydroxybenzoyl)pyrrole in 50 ml of anhydrous methylene chloride was treated dropwise, with stirring, with a solution of 2.135 g (13.3 mmol) of bromine in 20 ml of anhydrous methylene chloride. When the addition was complete the reaction mixture was maintained at room temperature for 30 minutes further. It was then poured into saturated sodium bicarbonate solution, the organic layer was separated and the aqueous layer extracted twice with methylene chloride. The combined extracts were dried and evaporated in vacuo. The residue was purified by repeated t.l.c., using hexane:ethyl acetate (80:20) for the first development and methylene chloride for the second. There were obtained 519 mg (17%) of the title compound, a compound according to Formula X wherein: W is O; R is H; X and Y are Br; and Z is H,, which was recrystallized from ethyl acetate-hexane (mp 231°–232° C.—Dec).

Anal. Calcd. for $C_{19}H_{23}Br_2NO_2$ (mw 457.197): Theoretical: C, 49.91; H, 5.07; N, 3.06, Found: C, 50.02; H, 5.00; N, 3.05.

15B. Formula X Where X and Y are Br and R is Lower Alkyl or Benzyl

Similarly, by following the procedure of part A above and substituting for 3-(3,5-di-t-butyl-4-hydroxybenzoyl)pyrrole the following starting materials:
N-methyl-3-(3,5-di-t-butyl-4-hydroxybenzoyl)pyrrole,
N-ethyl-3-(3,5-di-t-butyl-4-hydroxybenzoyl)pyrrole,
N-i-propyl-3-(3,5-di-t-butyl-4-hydroxybenzoyl)pyrrole,
N-butyl-3-(3,5-di-t-butyl-4-hydroxybenzoyl)pyrrole, and
N-benzyl-3-(3,5-di-t-butyl-4-hydroxybenzoyl)pyrrole,
there are obtained the following respective compounds:
N-methyl-2,3-dibromo-4-(3,5-di-t-butyl-4-hydroxybenzoyl)pyrrole,
N-ethyl-2,3-dibromo-4-(3,5-di-t-butyl-4-hydroxybenzoyl)pyrrole,
N-i-propyl-2,3-dibromo-4-(3,5-di-t-butyl-4-hydroxybenzoyl)pyrrole,
N-butyl-2,3-dibromo-4-(3,5-di-t-butyl-4-hydroxybenzoyl)pyrrole, and
N-benzyl-2,3-dibromo-4-(3,5-di-t-butyl-4-hydroxybenzoyl)pyrrole.

15C. Formula X Where X and Y are Br, m is 1–3 and n is 0–1

Similarly, by following the procedure of part A above and substituting for 3-(3,5-di-t-butyl-4-hydroxybenzoyl)pyrrole the following starting materials:
3-(3,5-di-t-butyl-4-hydroxybenzyl)pyrrole,
3-[3-(3,5-di-t-butyl-4-hydroxyphenyl)propyl]pyrrole,
3-[2-(3,5-di-t-butyl-4-hydroxyphenyl)-1-oxoethyl]pyrrole, and
3-[3-(3,5-di-t-butyl-4-hydroxyphenyl)-1-oxopropyl]pyrrole,
there may be obtained the following respective compounds:
2,3-dibromo-4-(3,5-di-t-butyl-4-hydroxybenzyl)pyrrole,
2,3-dibromo-4-[3-(3,5-di-t-butyl-4-hydroxyphenyl)-propyl]-pyrrole,
2,3-dibromo-4-[2-(3,5-di-t-butyl-4-hydroxyphenyl)-1-oxoethyl]pyrrole, and
2,3-dibromo-4-[3-(3,5-di-t-butyl-4-hydroxyphenyl)-1-oxopropyl]pyrrole.

15D. Formula X Where X and Y are Br, R is Other Than Methyl, m is 1–3 and n is 0–1

Similarly, by following the procedure of part A above and substituting for 3-(3,5-di-t-butyl-4-hydroxybenzoyl)pyrrole the following starting materials:
N-benzyl-3-(3,5-di-t-butyl-4-hydroxybenzyl)pyrrole, and
N-ethyl-3-[2-(3,5-di-t-butyl-4-hydroxyphenyl)-1-oxoethyl]pyrrole;
there may be obtained the following compounds:
N-benzyl-2,3-dibromo-4-(3,5-di-t-butyl-4-hydroxybenzyl)pyrrole, and
N-ethyl-2,3-dibromo-4-[2-(3,5-di-t-butyl-4-hydroxyphenyl)-1-oxoethyl]pyrrole.

15E. Formula X Where X and Y are I

Similarly, by following the procedure of part A above and substituting elemental iodine for elemental bromine, there is obtained 2,3-di-iodo-4-(3,5-di-t-butyl-4-hydroxybenzoyl)pyrrole, for which the variations described in parts B–D are equally applicable.

EXAMPLE 16

Synthesis of 2-thiocyano-4-(3,5-di-t-butyl-4-hydroxybenzoyl)pyrrole and 2,3-dithiocyano-4-(3,5-di-t-butyl-4-hydroxybenzoyl)pyrrole 16A. Formula X Where Y, and/or X is SCN A solution of thiocyanogen was prepared as follows: 3.895 g (40 mmol) of potassium thiocyanate was partially dissolved in 10 ml of anhydrous methanol, under heating. The mixture was cooled to 0° C. and 3.202 g (20 mmol) of bromine in 30 ml of methylene chloride was added dropwise, stirring for 30 minutes further at room temperature.

The resultant pale yellow solution of thiocyanogen was added dropwise, at room temperature, to a solution of 3 g (10 mmol) of 3-(3,5-di-t-butyl-4-hydroxybenzoyl)-pyrrole in 30 ml of anhydrous dimethylformamide; the resultant pale organge solution was kept at room temperature for 1 hour, poured into water and extracted with methylene chloride. The organic extract was dried and evaporated.

Column chromatography of the residue on 150 g of silica gel, using hexane:ethyl acetate (80:20) as eluant, afforded 2.328 g (65%) of 2-thiocyano-4-(3,5-di-t-butyl-4-hydroxybenzoyl)pyrrole, a compound according to Formula X wherein: m is 0; n is 1; R is H; X is SCN; and Y and Z are both H, (mp 230°–231° C.), as well as a less polar mixture.

This less polar mixture was submitted to column chromatography on 160 g of deactivated alumina (containing 3% water). The fraction eluted with hexane-ethyl acetate (80:20) afforded 300 mg (7.5%) of 2,3-dithiocyano-4-(3,5-di-t-butyl-4-hydroxybenzoyl)pyrrole, a compound according to Formula X wherein: m is 0; n is 1; R is H; X and Y are both SCN; and Z is H, (mp 143°–144° C.).

Both compounds were recrystallized from methylene chloride-hexane.

16B. Formula X Where Y and/or X is SCN and R is Lower Alkyl or Benzyl

Similarly, by following the procedure of part A above and substituting for 3-(3,5-di-t-butyl-4-hydroxybenzoyl)pyrrole the following starting materials:
N-methyl-3-(3,5-di-t-butyl-4-hydroxybenzoyl)pyrrole,
N-ethyl-3-(3,5-di-t-butyl-4-hydroxybenzoyl)pyrrole,
N-i-propyl-3-(3,5-di-t-butyl-4-hydroxybenzoyl)pyrrole,
N-butyl-3-(3,5-di-t-butyl-4-hydroxybenzoyl)pyrrole, and
N-benzyl-3-(3,5-di-t-butyl-4-hydroxybenzoyl)pyrrole,
there are obtained the following respective compounds:
N-methyl-3-(3,5-di-t-butyl-4-hydroxybenzoyl)-4-thiocyanopyrrole,
N-methyl-2,3-dithiocyano-4-(3,5-di-t-butyl-4-hydroxybenzoyl)pyrrole,
N-ethyl-3-(3,5-di-t-butyl-4-hydroxybenzoyl)-4-thiocyanopyrrole,
N-ethyl-2,3-dithiocyano-4-(3,5-di-t-butyl-4-hydroxybenzoyl)pyrrole,
N-i-propyl-3-(3,5-di-t-butyl-4-hydroxybenzoyl)-4-thiocyanopyrrole,
N-i-propyl-2,3-dithiocyano-4-(3,5-di-t-butyl-4-hydroxybenzoyl)pyrrole,
N-butyl-3-(3,5-di-t-butyl-4-hydroxybenzoyl)-4-thiocyanopyrrole,
N-butyl-2,3-dithiocyano-4-(3,5-di-t-butyl-4-hydroxybenzoyl)pyrrole,
N-benzyl-3-(3,5-di-t-butyl-4-hydroxybenzoyl)-4-thiocyanopyrrole, and
N-benzyl-2,3-dithiocyano-4-(3,5-di-t-butyl-4-hydroxybenzoyl)pyrrole.

16C. Formula X Where Y and/or X is SCN, m is 1–3 and n is 0–1

Similarly, by following the procedure of part A above and substituting for 3-(3,5-di-t-butyl-4-hydroxybenzoyl)pyrrole the following starting materials:
3-(3,5-di-t-butyl-4-hydroxybenzyl)pyrrole,
3-[3-(3,5-di-t-butyl-4-hydroxyphenyl)propyl]pyrrole,
3-[2-(3,5-di-t-butyl-4-hydroxyphenyl)-1-oxoethyl]pyrrole, and
3-[3-(3,5-di-t-butyl-4-hydroxyphenyl)-1-oxopropyl]pyrrole,
there are obtained the following respective compounds:
3-(3,5-di-t-butyl-4-hydroxybenzyl)-4-thiocyanopyrrole,
2,3-dithiocyano-4-(3,5-di-t-butyl-4-hydroxybenzyl)pyrrole,
3-[3-(3,5-di-t-butyl-4-hydroxyphenyl)propyl]-4-thiocyanopyrrole,
2,3-dithiocyano-4-[3-(3,5-di-t-butyl-4-hydroxyphenyl)propyl]pyrrole,
3-[2-(3,5-di-t-butyl-4-hydroxyphenyl)-1-oxoethyl]-4-thiocyanopyrrole,
2,3-dithiocyano-4-[2-(3,5-di-t-butyl-4-hydroxyphenyl)-1-oxoethyl]pyrrole
3-[3-(3,5-di-t-butyl-4-hydroxyphenyl)-1-oxopropyl]-4-thiocyanopyrrole, and
2,3-dithiocyano-4-[3-(3,5-di-t-butyl-4-hydroxyphenyl)-1-oxopropyl]pyrrole.

16D. Formula X Where Y and/or X is SCN, R is Other Than Methyl, m is 1–3 and n is 0–1

Similarly, by following the procedure of part A above and substituting for 3-(3,5-di-t-butyl-4-hydroxybenzoyl)pyrrole the following starting materials:
N-benzyl-3-(3,5-di-t-butyl-4-hydroxybenzyl)pyrrole, and
N-ethyl-3-[2-(3,5-di-t-butyl-4-hydroxyphenyl)-1-oxoethyl]pyrrole;
there are obtained the following compounds:
N-benzyl-3-(3,5-di-t-butyl-4-hydroxybenzyl)-4-thiocyanopyrrole,
N-benzyl-2,3-dithiocyano-4-(3,5-di-t-butyl-4-hydroxybenzyl)pyrrole,
N-ethyl-3-[2-(3,5-di-t-butyl-4-hydroxyphenyl)-1-oxoethyl]-4-thiocyanopyrrole, and
N-ethyl-2,3-dithiocyano-4-[2-(3,5-di-t-butyl-4-hydroxyphenyl)-1-oxoethyl]pyrrole.

EXAMPLE 17

Synthesis of N-methyl-2-thiocyano-4-(3,5-di-t-butyl-4-hydroxybenzoyl)pyrrole

17A. Formula X Where R is Methyl and X is Thiocyano

N-methyl-(3,5-di-t-butyl-4-hydroxybenzoyl)pyrrole (8 g) was dissolved in methanol (50 ml) and cooled to −70° C. A solution of thiocyanogen was prepared by the dropwise addition of a cold (−70° C.) solution of bromine (6.6 g) in methanol (20 ml) to a solution of potassium thiocyanate (5.2 g) in methanol (20 ml) (also cooled to −70° C.). The resulting solution of thiocyanogen was added in one portion to the cold solution of the pyrrole. The reaction mixture was allowed to warm to −40° C. and was stirred for 30 minutes, keeping the temperature between −40° C. and −30° C. The solution was added to ice water and the crude product precipitated as a gum.

After decanting the water, the gum was washed well with water and then dissolved in methylene chloride, dried over sodium sulfate, and the solvent was evaporated. The residue was chromatographed on silica gel (500 g), eluting with hexane:ethyl-acetate (80:20) to yield 2.85 g of the title compound as a foam [$^1$H nmr: 1.5s (18H), 3.86s (3H), 5.68s (OH), 7.13d (1H), 7.53d (1H), 7.77s (2H); MS m/e 370 (M+)].

17B. Formula X Where X is Thiocyano and R is Benzyl or Lower Alkyl Other Than Methyl Similarly, by following the procedure of part A above and substituting for N-methyl-3-(3,5-di-t-butyl-4-hydroxybenzoyl)pyrrole the following starting materials:
N-ethyl-3-(3,5-di-t-butyl-4-hydroxybenzoyl)pyrrole,
N-i-propyl-3-(3,5-di-t-butyl-4-hydroxybenzoyl)pyrrole, N-butyl-3-(3,5-di-t-butyl-4-hydroxybenzoyl)pyrrole, and
N-benzyl-3-(3,5-di-t-butyl-4-hydroxybenzoyl)pyrrole,
there are obtained the following respective compounds:
N-ethyl-2-thiocyano-4-(3,5-di-t-butyl-4-hydroxybenzoyl)pyrrole,
N-i-propyl-2-thiocyano-4-(3,5-di-t-butyl-4-hydroxybenzoyl)pyrrole,
N-butyl-2-thiocyano-4-(3,5-di-t-butyl-4-hydroxybenzoyl)pyrrole, and
N-benzyl-2-thiocyano-4-(3,5-di-t-butyl-4-hydroxybenzoyl)pyrrole.

17C. Formula X Where R is Methyl, X is SCN, m is 1-3 and n is 0-1

Similarly, by following the procedure of part A above and substituting for N-methyl-3-(3,5-di-t-butyl-4-hydroxybenzoyl)pyrrole the following starting materials:
N-methyl-3-(3,5-di-t-butyl-4-hydroxybenzyl)pyrrole,
N-methyl-3-[3-(3,5-di-t-butyl-4-hydroxyphenyl)propyl]pyrrole,
N-methyl-3-[2-(3,5-di-t-butyl-4-hydroxyphenyl)-1-oxoethyl]pyrrole, and
N-methyl-3-[3-(3,5-di-t-butyl-4-hydroxyphenyl)-1-oxopropyl]pyrrole,
there are obtained the following respective compounds:
N-methyl-2-thiocyano-4-(3,5-di-t-butyl-4-hydroxybenzyl)pyrrole,
N-methyl-2-thiocyano-4-[3-(3,5-di-t-butyl-4-hydroxyphenyl)propyl]pyrrole,
N-methyl-2-thiocyano-4-[2-(3,5-di-t-butyl-4-hydroxyphenyl)-1-oxoethyl]pyrrole, and
N-methyl-2-thiocyano-4-[3-(3,5-di-t-butyl-4-hydroxyphenyl)-1-oxopropyl]pyrrole.

EXAMPLE 18

Synthesis of 2-mercapto-4-(3,5-di-t-butyl-4-hydroxybenzoyl)pyrrole

18A. Formula X Where X is Mercapto

2-Thiocyano-4-(3,5-di-t-butyl-4-hydroxybenzoyl)pyrrole (10.0 g) was dissolved in methanol (80 ml) and cooled to −10° C. Potassium hydroxide (3.2 g) in methanol (20.0 ml) and water (20.0 ml) was added at such a rate that the temperature did not exceed 0° C. After stirring for 1 hour at the same temperature, one half of the resulting solution was converted to the title compound by acidification with 20% HCl. The product was filtered, dissolved in methylene chlorede, dried and the solvent evaporated to dryness. The residue was chromatographed on silica gel (500 g) and the product eluted with hexane:ethyl acetate (1:1) to yield 1.56 g of the purified title compound, 2-mercapto-4-(3,5-di-t-butyl-4-hydroxybenzoyl)pyrrole, after recrystalization from ethyl acetate-hexane [mp 213°–215° C.; $^1$H nmr: 1.46s (18H), 5.46s (OH), 6.93m (1H), 7.46m (1H), 7.76s (2H), 7.91 (NH); MS m/e 331 (M+)].

Analysis calculated for $C_{19}H_{25}NO_2S$ (mw 331.45): Theoretical: C, 68.84; H, 7.60; N, 4.22, Found: C, 69.04; H, 7.38; N, 4.16.

18B. Formula X Where X, Y and/or Z is Mercapto

Similarly, by following the procedure of part A above and substituting for 2-thiocyano-4-(3,5-di-t-butyl-4-hydroxybenzoyl)pyrrole the following starting materials:
3-(3,5-di-t-butyl-4-hydroxybenzoyl)-4-thiocyanopyrrole,
2,3-dithiocyano-4-(3,5-di-t-butyl-4-hydroxybenzoyl)pyrrole, and
2,3,5-trithiocyano-4-(3,5-di-t-butyl-4-hydroxybenzoyl)pyrrole;
there are obtained the following compounds:
3-mercapto-4-(3,5-di-t-butyl-4-hydroxybenzoyl)pyrrole,
2,3-dimercapto-4-(3,5-di-t-butyl-4-hydroxybenzoyl)pyrrole, and
2,3,5-trimercapto-4-(3,5-di-t-butyl-4-hydroxybenzoyl)pyrrole.

18C. Formula X Where X is Mercapto and R is Lower Alkyl or Benzyl

Similarly, by following the procedure of part A above and substituting for 2-thiocyano-4-(3,5-di-t-butyl-4-hydroxybenzoyl)pyrrole the following starting materials:
N-methyl-2-thiocyano-4-(3,5-di-t-butyl-4-hydroxybenzoyl)pyrrole,
N-ethyl-2-thiocyano-4-(3,5-di-t-butyl-4-hydroxybenzoyl)pyrrole,
N-i-propyl-2-thiocyano-4-(3,5-di-t-butyl-4-hydroxybenzoyl)pyrrole,
N-butyl-2-thiocyano-4-(3,5-di-t-butyl-4-hydroxybenzoyl)pyrrole, and
N-benzyl-2-thiocyano-4-(3,5-di-t-butyl-4-hydroxybenzoyl)pyrrole;
there are obtained the following respective compounds:
N-methyl-2-mercapto-4-(3,5-di-t-butyl-4-hydroxybenzoyl)pyrrole,
N-ethyl-2-mercapto-4-(3,5-di-t-butyl-4-hydroxybenzoyl)pyrrole,
N-i-propyl-2-mercapto-4-(3,5-di-t-butyl-4-hydroxybenzoyl)pyrrole,
N-butyl-2-mercapto-4-(3,5-di-t-butyl-4-hydroxybenzoyl)pyrrole, and
N-benzyl-2-mercapto-4-(3,5-di-t-butyl-4-hydroxybenzoyl)pyrrole.

18D. Formula X Where X, Y and/or Z is Mercapto, R is H, Lower Alkyl or Benzyl, m is 1-3 and n is 0-1

Similarly, by following the procedure of part A above and substituting for 2-thiocyano-4-(3,5-di-t-butyl-4-hydroxybenzoyl)pyrrole the following starting materials:
2-thiocyano-4-(3,5-di-t-butyl-4-hydroxybenzyl)pyrrole,
N-ethyl-2,3-dithiocyano-4-(3,5-di-t-butyl-4-hydroxybenzyl)pyrrole,
N-methyl-2-thiocyano-4-[3-(3,5-di-t-butyl-4-hydroxyphenyl)propyl]pyrrole,
N-benzyl-2-thiocyano-4-[2-(3,5-di-t-butyl-4-hydroxyphenyl)-1-oxoethyl]pyrrole, and
N-methyl-2-thiocyano-4-[3-(3,5-di-t-butyl-4-hydroxyphenyl)-1-oxopropyl]pyrrole;
there are obtained the following respective compounds:
2-mercapto-4-(3,5-di-t-butyl-4-hydroxybenzyl)pyrrole,
N-ethyl-2,3-dimercapto-4-(3,5-di-t-butyl-4-hydroxybenzyl)pyrrole,
N-methyl-2-mercapto-4-[3-(3,5-di-t-butyl-4-hydroxyphenyl)propyl]pyrrole,
N-benzyl-2-mercapto-4-[2-(3,5-di-t-butyl-4-hydroxyphenyl)-1-oxoethyl]pyrrole, and
N-methyl-2-mercapto-4-[3-(3,5-di-t-butyl-4-hydroxyphenyl)-1-oxopropyl]pyrrole.

EXAMPLE 19

Synthesis of 2-ethylthio-4-(3,5-di-t-butyl-4-hydroxybenzoyl)pyrrole

19A. Formula X Where X is Ethylthio

2-Thiocyano-4-(3,5-di-t-butyl-4-hydroxybenzoyl)pyrrole (2.0 g) was dissolved in ethanol (20 ml) and ethyl iodide (0.8 ml) was added with stirring. The reaction mixture was cooled to −5° C. and a solution of potassium hydroxide (6.39 g) in water (5.0 ml) was added dropwise, at such a rate that the temperature did not exceed 0° C. After stirring for 1 additional hour, the reaction mixture was poured into 10% HCl (200 ml) and extracted with ethyl acetate (3×200 ml). The organic phase was washed with water (2×150 ml), dried and evaporated. The residue was purified by chromatography on alumina (3% water, 200 g) with hexane:acetone (80:20) to give 1.37 g of the pure product, which was crystallized from acetone-hexane [mp 197°–199° C.; $^1$H nmr: 1.23t (3H), 1.50s (18H), 2.66c (2H), 5.63s (OH), 6.86m (1H), 7.41m (1H), 7.81s (2H), 9.36 (NH)].

Analysis calculated for $C_{21}H_{29}NO_2S$ (mw 359.50): Theoretical: C, 70.15; H, 8.13; N, 3.89, Found: C, 70.12; H, 8.18; N, 3.90.

19B. Formula X Where X, Y and/or Z is Ethylthio

Similarly, by following the procedure of part A above and substituting for 2-thiocyano-4-(3,5-di-t-butyl-4-hydroxybenzoyl)pyrrole the following starting materials:
3-(3,5-di-t-butyl-4-hydroxybenzoyl)-4-thiocyanopyrrole,
2,5-dithiocyano-4-(3,5-di-t-butyl-4-hydroxybenzoyl)pyrrole, and
2,3,5-trithiocyano-4-(3,5-di-t-butyl-4-hydroxybenzoyl)pyrrole;
there are obtained the following compounds:
3-ethylthio-4-(3,5-di-t-butyl-4-hydroxybenzoyl)pyrrole,
2,5-diethylthio-4-(3,5-di-t-butyl-4-hydroxybenzoyl)pyrrole, and
2,3,5-triethylthio-4-(3,5-di-t-butyl-4-hydroxybenzoyl)pyrrole.

19C. Formula X Where X is Ethylthio and R is Lower Alkyl or Benzyl

Similarly, by following the procedure of part A above and substituting for 2-thiocyano-4-(3,5-di-t-butyl-4-hydroxybenzoyl)pyrrole the following starting materials:
N-methyl-2-thiocyano-4-(3,5-di-t-butyl-4-hydroxybenzoyl)pyrrole,
N-ethyl-2-thiocyano-4-(3,5-di-t-butyl-4-hydroxybenzoyl)pyrrole,
N-i-propyl-2-thiocyano-4-(3,5-di-t-butyl-4-hydroxybenzoyl)pyrrole,
N-butyl-2-thiocyano-4-(3,5-di-t-butyl-4-hydroxybenzoyl)pyrrole, and
N-benzyl-2-thiocyano-4-(3,5-di-t-butyl-4-hydroxybenzoyl)pyrrole;
there are obtained the following respective compounds:
N-methyl-2-ethylthio-4-(3,5-di-t-butyl-4-hydroxybenzoyl)pyrrole,
N-ethyl-2-ethylthio-4-(3,5-di-t-butyl-4-hydroxybenzoyl)pyrrole,
N-i-propyl-2-ethylthio-4-(3,5-di-t-butyl-4-hydroxybenzoyl)pyrrole,
N-butyl-2-ethylthio-4-(3,5-di-t-butyl-4-hydroxybenzoyl)pyrrole, and
N-benzyl-2-ethylthio-4-(3,5-di-t-butyl-4-hydroxybenzoyl)pyrrole.

19D. Formula X Where X, Y and/or Z is Ethylthio, R is H, Lower Alkyl or Benzyl, m is 1–3 and n is 0–1

Similarly, by following the procedure of part A above and substituting for 2-thiocyano-3-(3,5-di-t-butyl-4-hydroxybenzoyl)pyrrole the following starting materials:
2-thiocyano-4-(3,5-di-t-butyl-4-hydroxybenzyl)pyrrole,
N-ethyl-2,3-dithiocyano-4-(3,5-di-t-butyl-4-hydroxybenzyl)pyrrole,
N-methyl-2-thiocyano-4-[3-(3,5-di-t-butyl-4-hydroxyphenyl)propyl]pyrrole,
N-benzyl-2-thiocyano-4-[2-(3,5-di-t-butyl-4-hydroxyphenyl)-1-oxoethyl]pyrrole, and
N-methyl-2-thiocyano-4-[3-(3,5-di-t-butyl-4-hydroxyphenyl)-1-oxopropyl]pyrrole;
there are obtained the following respective compounds:
2-ethylthio-4-(3,5-di-t-butyl-4-hydroxybenzyl)pyrrole,
N-ethyl-2,3-diethylthio-4-(3,5-di-t-butyl-4-hydroxybenzyl)pyrrole,
N-methyl-2-ethylthio-4-[3-(3,5-di-t-butyl-4-hydroxyphenyl)propyl]pyrrole,
N-benzyl-2-ethylthio-4-[2-(3,5-di-t-butyl-4-hydroxyphenyl)-1-oxoethyl]pyrrole, and
N-methyl-2-ethylthio-4-[3-(3,5-di-t-butyl-4-hydroxyphenyl)-1-oxopropyl]pyrrole.

19E. Formula X Where X is Methylthio and R is Lower Alkyl

Similarly, by following the procedure of part A above and substituting N-methyl-2-thiocyano-4-(3,5-di-t-butyl-4-hydroxybenzoyl)pyrrole for 2-thiocyano-4-(3,5-di-t-butyl-4-hydroxybenzoyl)pyrrole, and substituting methyl iodide for ethyl iodide, there is obtained N-methyl-2-methylthio-4-(3,5-di-t-butyl-4-hydroxybenzoyl)pyrrole [mp 173°–175° C.; $^1$H nmr: 1.50s (18H), 2.3s (3H), 3.73s (3H), 5.6s (OH), 6.81m (1H), 7.38m (1H), 7.76s (2H)].

Analysis calculated for $C_{21}H_{29}NO_2S$ (mw 359.50): Theoretical: C, 70.15; H, 8.13; N, 3.89, Found: C, 69.77; H, 8.15; N, 3.75.

EXAMPLE 20

Synthesis of 3-methylthio-4-(3,5-di-t-butyl-4-hydroxybenzoyl)pyrrole

Formula Z Where Y is Methylthio

A solution of 1.51 g (4.23 mmol) of 3-(3,5-di-t-butyl-4-hydroxybenzoyl)-4-thiocyanopyrrole in 40 ml of anhydrous methanol was treated with 0.276 ml (630 mg, 4.4 mmol) of methyl iodide. The stirred mixture was cooled to −15° C. and a solution of 508 mg (12 mmol) of sodium hydroxide in 35 ml of methanol was added thereto, in a dropwise fashion. When the addition was completed the reaction mixture was kept at room temperature for 30 minutes. Dry ice was carefully added until a pH 8 was obtained. It was then poured into 200 ml of 20% sodium chloride solution, and the product extracted with methylene chloride; the extract was dried and evaporated under reduced pressure.

Purification of the residue by tlc using hexaneethyl acetate (70:30) afforded 1.51 g (73.5%) of the title compound, a compound according to Formula X wherein: m is 0; n is 1; R is H; Y is $SCH_3$; and X and Z are both H, which was recrystallized from ethyl acetate-hexane (mp 175°–176.5° C.)

EXAMPLE 21

Synthesis of
2,3-dimethylthio-4-(3,5-di-t-butyl-4-hydroxybenzoyl)-
pyrrole

Formula X Where X and Y are Methylthio

A stirred mixture of 0.9 ml (941 mg, 9.9 mmol) of methyl disulfide and 20 ml of anhydrous methylene chloride was treated dropwise, under nitrogen atmosphere, with 0.8 ml (1.349 g, 10 mmol) of sulfuryl chloride. The resulting mixture was kept at room temperature for 1 hour and then added dropwise, under stirring, to a solution of 2 g (6.6 mmol) of 3-(3,5-di-t-butyl-4-hydroxybenzoyl)pyrrole in 20 ml of anhydrous dimethylformamide. The deep brown reaction mixture was maintained for 1 additional hour at room temperature. It was then poured into water and extracted twice with methylene chloride. The combined extracts were dried and evaporated to dryness in vacuo.

Purificiation of the residue by tlc using hexane-ethyl acetate (80:20) gave 244 mg (9.5%) of the title compound, a compound according to Formula X wherein: m is 0; n is 1; R is H; Z is H; and X and Y are both $SCH_3$ (mp 222.5°–223° C.), which was recrystallized from methylene chloride-hexane.

EXAMPLE 22

Synthesis of
2-acetylthio-4-(3,5-di-t-butyl-4-hydroxybenzoyl)pyrrole

22A. Formula X Where X is Acetylthio

2-Thiocyano-4-(3,5-di-t-butyl-4-hydroxybenzoyl)-pyrrole (5.0 g) and sodium acetate (40.0 g) were dissolved in acetic acid (200 ml) and acetic anhydride (200 ml). With vigorous mechanical stirring, zinc dust (21 g) was added in 3 equal portions, one every 10 minutes. During this time the temperature rose from the initial 23° C., but stayed below 30° C. Vigorous stirring was continued for 1 hour more. Then ice water (1 l) was added and the reaction mixture was stirred for another 2 hours. The precipitated product was filtered, washed well with water and then dissolved in methylene chloride, dried and the solvent evaporated to dryness. The recovered product was crystallized from methylene chloride-methanol to give 3.42 g of the purified title compound 2-acetylthio-4-(3,5-di-t-butyl-4-hydroxybenzoyl)pyrrole (mp 223°–225° C.).

$^1H$ nmr: 1.48s (18H), 2.35s (3H), 5.78s (OH), 6.88m (1H), 7.55m (1H), 7.78s (2H), 11.00 (NH).

Analysis calculated for $C_{21}H_{27}NO_3S$ (mw 373.49): Theoretical: C, 67.52; H, 7.28; N, 3.74, Found: C, 67.83; H, 7.46; N, 3.70.

22B. Formula X Where X, Y and/or Z is Acetylthio

Similarly, by following the procedure of part A above and substituting for 2-thiocyano-4-(3,5-di-t-butyl-4-hydroxybenzoyl)pyrrole the following starting materials:

3-(3,5-di-t-butyl-4-hydroxybenzoyl)-4-thiocyanopyrrole,
2,5-dithiocyano-4-(3,5-di-t-butyl-4-hydroxybenzoyl)-pyrrole, and
2,3,5-trithiocyano-4-(3,5-di-t-butyl-4-hydroxybenzoyl)-pyrrole;

there are obtained the following compounds:
3-acetylthio-4-(3,5-di-t-butyl-4-hydroxybenzoyl)pyrrole,
2,5-diacetylthio-4-(3,5-di-t-butyl-4-hydroxybenzoyl)-pyrrole, and
2,3,5-triacetylthio-4-(3,5-di-t-butyl-4-hydroxybenzoyl)-pyrrole.

22C. Formula X Where X is Acetylthio and R is Lower Alkyl or Benzyl

Similarly, by following the procedure of part A above and substituting for 2-thiocyano-4-(3,5-di-t-butyl-4-hydroxybenzoyl)pyrrole the following starting materials:

N-methyl-2-thiocyano-4-(3,5-di-t-butyl-4-hydroxybenzoyl)pyrrole,
N-ethyl-2-thiocyano-4-(3,5-di-t-butyl-4-hydroxybenzoyl)pyrrole,
N-i-propyl-2-thiocyano-4-(3,5-di-t-butyl-4-hydroxybenzoyl)pyrrole,
N-butyl-2-thiocyano-4-(3,5-di-t-butyl-4-hydroxybenzoyl)pyrrole, and
N-benzyl-2-thiocyano-4-(3,5-di-t-butyl-4-hydroxybenzoyl)pyrrole;

there are obtained the following respective compounds:
N-methyl-2-acetylthio-4-(3,5-di-t-butyl-4-hydroxybenzoyl)pyrrole,
N-ethyl-2-acetylthio-4-(3,5-di-t-butyl-4-hydroxybenzoyl)pyrrole,
N-i-propyl-2-acetylthio-4-(3,5-di-t-butyl-4-hydroxybenzoyl)pyrrole,
N-butyl-2-acetylthio-4-(3,5-di-t-butyl-4-hydroxybenzoyl)pyrrole, and
N-benzyl-2-acetylthio-4-(3,5-di-t-butyl-4-hydroxybenzoyl)pyrrole.

22D. Formula X Where X, Y and/or Z is Acetylthio, R is H, Lower Alkyl or Benzyl, m is 1–3 and n is 0–1

Similarly, by following the procedure of part A above and substituting for 2-thiocyano-4-(3,5-di-t-butyl-4-hydroxybenzoyl)pyrrole the following starting materials:

2-thiocyano-4-(3,5-di-t-butyl-4-hydroxybenzyl)pyrrole,
N-ethyl-2,3-dithiocyano-4-(3,5-di-t-butyl-4-hydroxybenzyl)pyrrole,
N-methyl-2-thiocyano-4-[3-(3,5-di-t-butyl-4-hydroxyphenyl)propyl]pyrrole,
N-benzyl-2-thiocyano-4-[2-(3,5-di-t-butyl-4-hydroxyphenyl)-1-oxoethyl]pyrrole, and
N-methyl-2-thiocyano-4-[3-(3,5-di-t-butyl-4-hydroxyphenyl)-1-oxopropyl]pyrrole;

there are obtained the following respective compounds:
2-acetylthio-4-(3,5-di-t-butyl-4-hydroxybenzyl)pyrrole,
N-ethyl-2,3-diacetylthio-4-(3,5-di-t-butyl-4-hydroxybenzyl)pyrrole,
N-methyl-2-acetylthio-4-[3-(3,5-di-t-butyl-4-hydroxyphenyl)propyl]pyrrole,
N-benzyl-2-acetylthio-4-[2-(3,5-di-t-butyl-4-hydroxyphenyl)-1-oxoethyl]pyrrole, and
N-methyl-2-acetylthio-4-[3-(3,5-di-t-butyl-4-hydroxyphenyl)-1-oxopropyl]pyrrole.

22E. Formula X Where X is Propionylthio

Similarly, by following the procedure of part A above and substituting propionic acid for acetic acid, and substituting propionic anhydride for acetic anhydride, there is obtained 2-propionylthio-4-(3,5-di-t-butyl-4-hydroxybenzoyl)pyrrole, for which the variations described in parts B–D are equally applicable.

EXAMPLE 23

Synthesis of N-methyl-2-acetylthio-4-(3,5-di-t-butyl-4-hydroxybenzoyl)pyrrole

Formula X Where R is Methyl and X is Acetylthio

N-Methyl-2-thiocyano-4-(3,5-di-t-butyl-4-hydroxybenzoyl)pyrrole (2.69 g) and sodium acetate (21.0 g) were dissolved in acetic acid (100 ml) and acetic anhydride (100 ml). With vigorous mechanical stirring, zinc dust (11 g) was added in portions. After stirring for 90 minutes, the reaction mixture was poured into ice water (1 l). The solution was extracted with methylene chloride (4×300 ml). The combined organic layers wer washed with water (3×500 ml), dried and evaporated to give 2.8 g of the crude product.

The crude product was purified by preparative tlc on silica gel plates, eluting with hexane:ethyl acetate (75:25), and repurified in the same manner with 80:20 hexane:ethyl acetate. The recovered product (1.4 g) was crystallized from acetone-hexane to afford 0.77 g of the purified title compound, N-methyl-2-acetylthio-4-(3,5-di-t-butyl-4-hydroxybenzoyl)pyrrole [mp 120°–123° C.; $^1$H nmr: 1.5s (18H), 2.41s (3H), 3.63s (3H), 5.63s (OH), 6.91m (1H), 7.51m (1H), 7.8s (2H); MS m/e 387 (M+)].

EXAMPLE 24

Synthesis of 2-methylsulfinyl-4-(3,5-di-t-butyl-4-hydroxybenzoyl)pyrrole

24A. Formula X Where X is Methylsulfinyl

2-Methylthio-4-(3,5-di-t-butyl-4-hydroxybenzoyl)pyrrole (4.0 g) was dissolved in methylene chloride (100 ml) and cooled in ice. A solution of m-chloroperbenzoic acid (2.48 g) in methylene chloride (100 ml) was added dropwise with stirring. After stirring for an additional 30 minutes, the mixture was poured into a saturated sodium bicarbonate solution (200 ml). After separation of the organic layer, the aqueous phase was extracted with methylene chloride (300 ml) and then with ethyl acetate (300 ml). The combined organic extracts were dried and evaporated to dryness and the residue was recrystallized from methanol-methylene chloride to afford 4.10 g of the purified title product, 2-methylsulfinyl-4-(3,5-di-t-butyl-4-hydroxybenzoyl)pyrrole (a compound according to Formula X wherein: m is 0; n is 1; R is H; X is SOCH$_3$; and Y and Z are both H) (mp 201°–202.5° C.).

24B. Formula X Where X, Y and/or Z is Methylsulfinyl

Similarly, by following the procedure of part A above and substituting for 2-methylthio-4-(3,5-di-t-butyl-4-hydroxybenzoyl)pyrrole the following starting materials:

3-methylthio-4-(3,5-di-t-butyl-4-hydroxybenzoyl)pyrrole,
2,5-dimethylthio-4-(3,5-di-t-butyl-4-hydroxybenzoyl)pyrrole, and
2,3,5-trimethylthio-4-(3,5-di-t-butyl-4-hydroxybenzoyl)pyrrole;
there are obtained the following compounds:
3-methylsulfinyl-4-(3,5-di-t-butyl-4-hydroxybenzoyl)pyrrole,
2,5-dimethylsulfinyl-4-(3,5-di-t-butyl-4-hydroxybenzoyl)pyrrole, and
2,3,5-trimethylsulfinyl-4-(3,5-di-t-butyl-4-hydroxybenzoyl)pyrrole.

24C. Formula X Where X is Methylsulfinyl and R is Lower Alkyl or Benzyl

Similarly, by following the procedure of part A above and substituting for 2-methylthio-4-(3,5-di-t-butyl-4-hydroxybenzoyl)pyrrole the following starting materials:

N-methyl-2-methylthio-4-(3,5-di-t-butyl-4-hydroxybenzoyl)pyrrole,
N-ethyl-2-methylthio-4-(3,5-di-t-butyl-4-hydroxybenzoyl)pyrrole,
N-i-propyl-2-methylthio-4-(3,5-di-t-butyl-4-hydroxybenzoyl)pyrrole,
N-butyl-2-methylthio-4-(3,5-di-t-butyl-4-hydroxybenzoyl)pyrrole, and
N-benzyl-2-methylthio-4-(3,5-di-t-butyl-4-hydroxybenzoyl)pyrrole;
there are obtained the following respective compounds:
N-methyl-2-methylsulfinyl-4-(3,5-di-t-butyl-4-hydroxybenzoyl)pyrrole,
N-ethyl-2-methylsulfinyl-4-(3,5-di-t-butyl-4-hydroxybenzoyl)pyrrole,
N-i-propyl-2-methylsulfinyl-4-(3,5-di-t-butyl-4-hydroxybenzoyl)pyrrole,
N-butyl-2-methylsulfinyl-4-(3,5-di-t-butyl-4-hydroxybenzoyl)pyrrole, and
N-benzyl-2-methylsulfinyl-4-(3,5-di-t-butyl-4-hydroxybenzoyl)pyrrole.

24D. Formula X Where X, Y and/or Z is Methylsulfinyl, R is H, Lower Alkyl or Benzyl, m is 1–3 and n is 0–1

Similarly, by following the procedure of part A above and substituting for 2-methylthio-4-(3,5-di-t-butyl-4-hydroxybenzoyl)pyrrole the following starting materials:

2-methylthio-4-(3,5-di-t-butyl-4-hydroxybenzyl)-pyrrole,
N-ethyl-2,3-dimethylthio-4-(3,5-di-t-butyl-4-hydroxybenzyl)pyrrole,
N-methyl-2-methylthio-4-[3-(3,5-di-t-butyl-4-hydroxyphenyl)propyl]pyrrole,
N-benzyl-2-methylthio-4-[2-(3,5-di-t-butyl-4-hydroxyphenyl)-1-oxoethyl]pyrrole, and
N-methyl-2-methylthio-4-[3-(3,5-di-t-butyl-4-hydroxyphenyl)-1-oxopropyl]pyrrole;
there are obtained the following respective compounds:
2-methylsulfinyl-4-(3,5-di-t-butyl-4-hydroxybenzyl)pyrrole,
N-ethyl-2,3-dimethylsulfinyl-4-(3,5-di-t-butyl-4-hydroxybenzyl)pyrrole,
N-methyl-2-methylsulfinyl-4-[3-(3,5-di-t-butyl-4-hydroxyphenyl)propyl]pyrrole,
N-benzyl-2-methylsulfinyl-4-[2-(3,5-di-t-butyl-4-hydroxyphenyl)-1-oxoethyl]pyrrole, and
N-methyl-2-methylsulfinyl-4-[3-(3,5-di-t-butyl-4-hydroxyphenyl)-1-oxopropyl]pyrrole.

24E. Formula X Where X is Ethylsulfinyl

Similarly, by following the procedure of part A above and substituting 2-ethylthio-4-(3,5-di-t-butyl-4-hydroxybenzoyl)pyrrole for 2-methylthio-4-(3,5-di-t-butyl-4-hydroxybenzoyl)pyrrole, there is obtained 2-ethyl-sulfinyl-4-(3,5-di-t-butyl-4-hydroxybenzoyl)pyrrole, for which the variations described in parts 22B–D are equally applicable.

EXAMPLE 25

Synthesis of 2-methylsulfonyl-3-(3,5-di-t-butyl-4-hydroxybenzoyl)-pyrrole

25A. Formula X Where X is Methylsulfonyl

2-Methylsulfinyl-4-(3,5-di-t-butyl-4-hydroxybenzoyl)pyrrole (2.0 g) was dissolved in methylene chloride (40 ml) and a solution of m-chloroperbenzoic acid (1.2 g) was added. After stirring at room temperature for 30 minutes, the mixture was poured into a saturated sodium bicarbonate solution (100 ml). After separation of the organic layer, the aqueous phase was extracted with methylene chloride (300 ml). The combined organic extracts were dried and evaporated to dryness and the residue was recrystallized from ethyl acetate-hexane to afford 2.05 g of the purified title product, 2-methylsulfonyl-4-(3,5-di-t-butyl-4-hydroxybenzoyl)-pyrrole (a compound according to Formula X wherein: m is 0; n is 1; R is H; X is SO$_2$CH$_3$; and Y and Z are both H) (mp 237°–238° C.).

25B. Formula X Where X, Y and/or Z is Methylsulfonyl

Similarly, by following the procedure of part A above and substituting for 2-methylsulfinyl-4-(3,5-di-t-butyl-4-hydroxybenzoyl)pyrrole the following starting materials:
3-methylsulfinyl-4-(3,5-di-t-butyl-4-hydroxybenzoyl)-pyrrole,
2,5-dimethylsulfinyl-4-(3,5-di-t-butyl-4-hydroxybenzoyl)pyrrole, and
2,3,5-trimethylsulfinyl-4-(3,5-di-t-butyl-4-hydroxybenzoyl)pyrrole;
there are obtained the following compounds:
3-methylsulfonyl-4-(3,5-di-t-butyl-4-hydroxybenzoyl)-pyrrole,
2,5-dimethylsulfonyl-4-(3,5-di-t-butyl-4-hydroxybenzoyl)pyrrole, and
2,3,5-trimethylsulfonyl-4-(3,5-di-t-butyl-4-hydroxybenzoyl)pyrrole.

25C. Formula X Where X is Methylsulfonyl and R is Lower Alkyl or Benzyl

Similarly, by following the procedure of part A above and substituting for 2-methylsulfinyl-4-(3,5-di-t-butyl-4-hydroxybenzoyl)pyrrole the following starting materials:
N-methyl-2-methylsulfinyl-4-(3,5-di-t-butyl-4-hydroxybenzoyl)pyrrole,
N-ethyl-2-methylsulfinyl-4-(3,5-di-t-butyl-4-hydroxybenzoyl)pyrrole,
N-i-propyl-2-methylsulfinyl-4-(3,5-di-t-butyl-4-hydroxybenzoyl)pyrrole,
N-butyl-2-methylsulfinyl-4-(3,5-di-t-butyl-4-hydroxybenzoyl)pyrrole, and
N-benzyl-2-methylsulfinyl-4-(3,5-di-t-butyl-4-hydroxybenzoyl)pyrrole;
there are obtained the following respective compounds:
N-methyl-2-methylsulfonyl-4-(3,5-di-t-butyl-4-hydroxybenzoyl)pyrrole,
N-ethyl-2-methylsulfonyl-4-(3,5-di-t-butyl-4-hydroxybenzoyl)pyrrole,
N-i-propyl-2-methylsulfinyl-4-(3,5-di-t-butyl-4-hydroxybenzoyl)pyrrole,
N-butyl-2-methylsulfonyl-4-(3,5-di-t-butyl-4-hydroxybenzoyl)pyrrole, and
N-benzyl-2-methylsulfonyl-4-(3,5-di-t-butyl-4-hydroxybenzoyl)pyrrole.

25D. Formula X Where X, Y and/or Z is Methylsulfonyl, R is H, Lower Alkyl or Benzyl, m is 1–3 and n is 0–1

Similarly, by following the procedure of part A above and substituting for 2-methylsulfinyl-4-(3,5-di-t-butyl-4-hydroxybenzoyl)pyrrole the following starting materials:
2-methylsulfinyl-4-(3,5-di-t-butyl-4-hydroxybenzyl)pyrrole,
N-ethyl-2,3-dimethylsulfinyl-4-(3,5-di-t-butyl-4-hydroxybenzyl)pyrrole,
N-methyl-2-methylsulfinyl-4-[3-3,5-di-t-butyl-4-hydroxyphenyl)propyl]pyrrole,
N-benzyl-2-methylsulfinyl-4-[2-(3,5-di-t-butyl-4-hydroxyphenyl)-1-oxoethyl]pyrrole, and
N-methyl-2-methylsulfinyl-4-[3-(3,5-di-t-butyl-4-hydroxyphenyl)-1-oxopropyl]pyrrole.
there are obtained the following respective compounds:
2-methylsulfonyl-4-(3,5-di-t-butyl-4-hydroxybenzyl)-pyrrole,
N-ethyl-2,3-dimethylsulfonyl-4-(3,5-di-t-butyl-4-hydroxybenzyl)pyrrole,
N-methyl-2-methylsulfonyl-4-[3-(3,5-di-t-butyl-4-hydroxyphenyl)propyl]pyrrole,
N-benzyl-2-methylsulfonyl-4-[2-(3,5-di-t-butyl-4-hydroxyphenyl)-1-oxoethyl]pyrrole, and
N-methyl-2-methylsulfonyl-4-[3-(3,5-di-t-butyl-4-hydroxyphenyl)-1-oxopropyl]pyrrole.

25E. Formula X Where X is Ethylsulfonyl

Similarly, by following the procedure of part A above and substituting 2-ethylsulfinyl-4-(3,5-di-t-butyl-4-hydroxybenzoyl)pyrrole for 2-methylsulfinyl-4-(3,5-di-t-butyl-4-hydroxybenzoyl)pyrrole, there is obtained 2-ethylsulfonyl-4-(3,5-di-t-butyl-4-hydroxybenzoyl)pyrrole, for which the variations described in parts 23B–D are equally applicable.

EXAMPLE 26

Synthesis of 2-methylsulfonyl-4-(3,5-di-t-butyl-4-hydroxybenzoyl)-pyrrole

26A. Formula X Where X is Methylsulfonyl

2-Methylthio-4-(3,5-di-t-butyl-4-hydroxybenzoyl)-pyrrole (4.0 g) is dissolved in methylene chloride (100 ml) and cooled in ice. A solution of m-chloroperbenzoic acid (5.0 g) in methylene chloride (100 ml) is added dropwise with stirring. After stirring for an additional 2 hours, the mixture is poured into a saturated sodium bicarbonate solution (200 ml). After separation of the organic layer, the aqueous phase is extracted with methylene chloride (300 ml) and then with ehtyl acetate (300 ml). The combined organic extracts are dried and evaporated to dryness and the residue is recrystallized from methanol-methylene chloride to afford the purified title product, 2-methylsulfonyl-4-(3,5-di-t-butyl-4-hydroxybenzoyl)pyrrole (a compound according to Formula X wherein: m is 0; n is 1; R is H; X is SO$_2$CH$_3$; and Y and Z are both H).

26B. Formula X Where X, Y and/or Z is Methylsulfonyl

Similarly, by following the procedure of part A above and substituting for 2-methylthio-4-(3,5-di-t-butyl-4-hydroxybenzoyl)pyrrole the following starting materials:
3-methylthio-4-(3,5-di-t-butyl-4-hydroxybenzoyl)pyrrole, 2,5-dimethylthio-4-(3,5-di-t-butyl-4-hydroxybenzoyl)-pyrrole, and
2,3,5-trimethylthio-4-(3,5-di-t-butyl-4-hydroxybenzoyl)pyrrole;
there are obtained the following compounds:
3-methylsulfonyl-4-(3,5-di-t-butyl-4-hydroxybenzoyl)-pyrrole,
2,5-dimethylsulfonyl-4-(3,5-di-t-butyl-4-hydroxybenzoyl)pyrrole, and
2,3,5-trimethylsulfonyl-4-(3,5-di-t-butyl-4-hydroxybenzoyl)pyrrole.

26C. Formula X Where X is Methylsulfonyl and R is Lower Alkyl or Benzyl

Similarly, by following the procedure of part A above and substituting for 2-methylthio-4-(3,5-di-t-butyl-4-hydroxybenzoyl)pyrrole the following starting materials:
N-methyl-2-methylthio-4-(3,5-di-t-butyl-4-hydroxybenzoyl)pyrrole,
N-ethyl-2-methylthio-4-(3,5-di-t-butyl-4-hydroxybenzoyl)pyrrole,
N-i-propyl-2-methylthio-4-(3,5-di-t-butyl-4-hydroxybenzoyl)pyrrole,
N-butyl-2-methylthio-4-(3,5-di-t-butyl-4-hydroxybenzoyl)pyrrole, and
N-benzyl-2-methylthio-4-(3,5-di-t-butyl-4-hydroxybenzoyl)pyrrole;
there are obtained the following respective compounds:
N-methyl-2-methylsulfonyl-4-(3,5-di-t-butyl-4-hydroxybenzoyl)pyrrole,
N-ethyl-2-methylsulfonyl-4-(3,5-di-t-butyl-4-hydroxybenzoyl)pyrrole,
N-i-propyl-2-methylsulfonyl-4-(3,5-di-t-butyl-4-hydroxybenzoyl)pyrrole,
N-butyl-2-methylsulfonyl-4-(3,5-di-t-butyl-4-hydroxybenzoyl)pyrrole, and
N-benzyl-2-methylsulfonyl-4-(3,5-di-t-butyl-4-hydroxybenzoyl)pyrrole.

26D. Formula X Where X, Y and/or Z is Methylsulfonyl, R is H, Lower Alkyl or Benzyl, m is 1-3 and n is 0-1

Similarly, by following the procedure of part A above and substituting for 2-methylthio-4-(3,5-di-t-butyl-4-hydroxybenzoyl)pyrrole the following starting materials:
2-methylthio-4-(3,5-di-t-butyl-4-hydroxybenzyl)pyrrole,
N-ethyl-2,3-dimethylthio-4-(3,5-di-t-butyl-4-hydroxybenzyl)pyrrole,
N-methyl-2-methylthio-4-[3-(3,5-di-t-butyl-4-hydroxyphenyl)propyl]pyrrole,
N-benzyl-2-methylthio-4-[2-(3,5-di-t-butyl-4-hydroxyphenyl)-1-oxoethyl]pyrrole, and
N-methyl-2-methylthio-4-[3-(3,5-di-t-butyl-4-hydroxyphenyl)-1-oxopropyl]pyrrole;
there are obtained the following respective compounds:
2-methylsulfonyl-4-(3,5-di-t-butyl-4-hydroxybenzyl)-pyrrole,
N-ethyl-2,3-dimethylsulfonyl-4-(3,5-di-t-butyl-4-hydroxybenzyl)pyrrole,
N-methyl-2-methylsulfonyl-4-[3-(3,5-di-t-butyl-4-hydroxyphenyl)propyl]pyrrole,
N-benzyl-2-methylsulfonyl-4-[2-(3,5-di-t-butyl-4-hydroxyphenyl)-1-oxoethyl]pyrrole, and
N-methyl-2-methylsulfonyl-4-[3-(3,5-di-t-butyl-4-hydroxyphenyl)-1-oxopropyl]pyrrole.

26E. Formula X Where X is Ethylsulfonyl

Similarly, by following the procedure of part A above and substituting 2-ethylthio-4-(3,5-di-t-butyl-4-hydroxybenzoyl)pyrrole for 2-methylthio-4-(3,5-di-t-butyl-4-hydroxybenzoyl)pyrrole, there is obtained 2-ethylsulfonyl-4-(3,5-di-t-butyl-4-hydroxybenzoyl)pyrrole, for which the variations described in parts 24B-D are equally applicable.

EXAMPLE 27

Synthesis of 3-(3,5-di-t-butyl-4-hydroxybenzyl)pyrrole

27A. Formula X Where m is 1 and n is 0

A solution of 1 g (3 mmol) of 3-(3,5-di-t-butyl-4-hydroxybenzoyl)pyrrole in 100 ml of anhydrous tetrahydrofuran was treated portionwise with 1 g (26 mmol) of lithium aluminum hydride. The reaction mixture was refluxed for 4 hours, cooled and poured into saturated sodium chloride solution. It was then extracted twice with methylene chloride. The combined extracts were dried and evaporated under reduced pressure.

The solid residue was purified on a chromatotron using hexane-ethyl acetate (80:20), to afford 935 mg (98%) of the title compound, a compound according to Formula X wherein: W is $H_2$; R is H; X, Y and Z are each H, which was recrystallized from hexane-pentane (mp 77.5°-78° C.).

Analysis Calculated for $C_{19}H_{27}NO$ (mw 285.417): Theoretical: C, 79.94; H, 9.53; N, 4.90. Found: C, 79.86; H, 9.51; N, 4.85.

27B. Formula X Where m is 2-3 and n is 0

Similarly, by following the procedure of part A above and substituting for 3-(3,5-di-t-butyl-4-hydroxybenzoyl)pyrrole the following starting materials:
3-[2-(3,5-di-t-butyl-4-hydroxyphenyl)-1-oxoethyl]pyrrole, and
3-[3-(3,5-di-t-butyl-4-hydroxyphenyl)-1-oxopropyl]pyrrole;
there are obtained the following respective compounds:
3-[2-(3,5-di-t-butyl-4-hydroxyphenyl)ethyl]pyrrole, and
3-[3-(3,5-di-t-butyl-4-hydroxyphenyl)propyl]pyrrole.

27C. Formula X Where m is 1-3, n is 0, and R is Lower Alkyl or Benzyl

Similarly, by following the procedure of part A above and substituting for 3-(3,5-di-t-butyl-4-hydroxybenzoyl)pyrrole the following starting materials:
N-methyl-3-(3,5-di-t-butyl-4-hydroxybenzoyl)pyrrole,
N-ethyl-3-[2-(3,5-di-t-butyl-4-hydroxyphenyl)-1-oxoethyl]pyrrole,
N-i-propyl-3-(3,5-di-t-butyl-4-hydroxybenzoyl)pyrrole,
N-s-butyl-3-[3-(3,5-di-t-butyl-4-hydroxyphenyl)-1-oxopropyl]pyrrole; and
N-benzyl-3-(3,5-di-t-butyl-4-hydroxybenzoly)pyrrole,
there are obtained the following respective compounds:
N-methyl-3-(3,5-di-t-butyl-4-hydroxybenzyl)pyrrole,
N-ethyl-3-[2-(3,5-di-t-butyl-4-hydroxyphenyl)ethyl]pyrrole,
N-i-propyl-3-(3,5-di-t-butyl-4-hydroxybenzyl)pyrrole,
N-s-butyl-3-[3-(3,5-di-t-butyl-4-hydroxyphenyl)propyl]pyrrole; and
N-benzyl-3-(3,5-di-t-butyl-4-hydroxybenzyl)pyrrole.

27D. Formula X Where m is 1-3, n is 0, R is Hydrogen, Lower Alkyl or Benzyl, and X, Y and/or Z is Lower Alkyl Similarly, by following the procedure of part A above and substituting for 3-(3,5-di-t-butyl-4-hydroxybenzoyl)pyrrole the following starting materials:
2,5-dimethyl-3-(3,5-di-t-butyl-4-hydroxybenzoyl)pyrrole, N-ethyl-2-ethyl-4-[2-(3,5-di-t-butyl-4-hydroxyphenyl)-1-oxoethyl]pyrrole, and N-benzyl-3-methyl-4-[3-(3,5-di-t-butyl-4-hydroxyphenyl)-1-oxopropyl]pyrrole;

there are obtained the following respective compounds:
2,5-dimethyl-3-(3,5-di-t-butyl-4-hydroxybenzyl)pyrrole, N-ethyl-2-ethyl-4-[2-(3,5-di-t-butyl-4-hydroxyphenyl)ethyl]pyrrole, and N-benzyl-3-methyl-4-[3-(3,5-di-t-butyl-4-hydroxyphenyl)propyl]pyrrole.

27E. Formula X Where m is 1–3, n is 0, R is Hydrogen, Lower Alkyl or Benzyl, and X, Y and/or Z is Halo Similarly, by following the procedure of part A above and substituting for 3-(3,5-di-t-butyl-4-hydroxybenzoyl)pyrrole the following starting materials:
2,3-dibromo-4-(3,5-di-t-butyl-4-hydroxybenzoyl)pyrrole, N-methyl-2-chloro-4-[2-(3,5-di-t-butyl-4-hydroxyphenyl)-1-oxoethyl]pyrrole, and N-benzyl-2,5-dichloro-4-[3-(3,5-di-t-butyl-4-hydroxyphenyl)-1-oxopropyl]pyrrole;

there are obtained the following respective compounds:
2,3-dibromo-4-(3,5-di-t-butyl-4-hydroxybenzyl)pyrrole,
N-methyl-2-chloro-4-[2-(3,5-di-t-butyl-4-hydroxyphenyl)ethyl]pyrrole, and
N-benzyl-2,5-dichloro-4-[3-(3,5-di-t-butyl-4-hydroxyphenyl)propyl]pyrrole.

27F. Formula X Where m is 1–3, n is 0, R is Hydrogen, Lower Alkyl, or Benzyl, and X, Y and/or Z is Mercapto or Lower Alkylthio Similarly, by following the procedure of part A above and substituting for 3-(3,5-di-t-butyl-4-hydroxybenzoyl)pyrrole the following starting materials:
2-mercapto-4-(3,5-di-t-butyl-4-hydroxybenzoyl)pyrrole, and
3-methylthio-4-(3,5-di-t-butyl-4-hydroxybenzoyl)pyrrole;

there are obtained the following respective compounds:
2-mercapto-4-(3,5-di-t-butyl-4-hydroxybenzyl)pyrrole, and
3-methylthio-4-(3,5-di-t-butyl-4-hydroxybenzyl)pyrrole.

EXAMPLE 28

Synthesis of
3-(3,5-di-t-butyl-4-hydroxybenzoyl)pyrrole-N-acetic acid

28A. Formula X Where R is $CH_2COOH$ 3-(3,5-di-t-butyl-4-hydroxybenzoyl)pyrrole (2.0 g) was added to a cooled, stirred suspension of sodium hydride (50%, 1.02 g) in DMF (90.0 ml) under nitrogen. After stirring for 1 hour at 20°–23° C., bromoacetic acid (1.12 g) was added and the mixture was stirred at room temperature for 20 hours. The mixture was poured into ice water (300 ml) and concentrated HCl (4.0 ml) was added. Then, the reaction mixture was extracted with ethyl acetate (3×250 ml). The organic layer was washed with water (5×200 ml), dried and evaporated to dryness. The product was isolated by conventional means, and obtained as an oil.

28B. Formula X Where R is $(CH_2)_2COOH$

Similarly, by following the procedure of part A above and substituting chloropropionic acid for bromoacetic acid, there is obtained 3-(3,5-di-t-butyl-4-hydroxybenzoyl)pyrrole-N-propionic acid.

EXAMPLE 29

Synthesis of
3-(3,5-di-t-butyl-4-hydroxybenzoyl)pyrrole-N-acetic acid dicyclohexylamine salt 29A. The Dicyclohexylamine Salt of Formula X Where R is $CH_2COOH$ The product obtained as an oil in Example 26A was converted to its dicyclohexylamine salt directly by dissolving the acid in methylene chloride (50.0 ml) and adding dicyclohexylamine (1.4 ml). Upon evaporation to dryness, the residue was recrystallized from ethyl acetate-hexane to give 2.1 g of the purified desired product. An analytical sample was prepared by recrystallization from methanol-ethyl acetate (mp 178°–179° C.).

$^1H$ nmr: 1.48m (18H), 4.46s (2H), 5.6s (OH), 6.65m (2H), 7.26m (1H), 7.80s (2H).

Anal. Calcd. for $C_{33}H_{50}N_2O_4$ (mw 547.76): Theoretical: C, 72.35; H, 8.90. Found: C, 72.27; H, 8.59.

EXAMPLE 30

Adjuvant-Induced Arthritis Assay "AI"

Anti-inflammatory activity is determined by the Adjuvant-Induced Arthritis ("AI") Assay, as is well accepted in the art. A modification of the assay described by Pearson, et al., supra., is performed as follows:

Female Hla:(SD) BR rats weighting 160–180 g are randomly distributed to treatment groups of 12 animals, and given food and water ad libitum. Test materials are prepared fresh weekly as suspensions in carboxymethyl cellulose. The test animals are orally dosed with the suspensions in volumes of 1 ml twice per day Monday through Friday, and with 2 ml once per day on Saturdays and Sundays. A control group does not receive the test materials. At time 0, rats are injected intradermally in the proximal quarter of the tail with 0.1 ml of a mineral oil suspension of heat-killed *Mycobacterium butyricum* (Difco) at a concentration of 10 mg/ml. On day 18 the intensity of swelling in the four paws and tail is estimated visually and scored (0–4 for paws, 0–3 for tail) such that the total maximum score, indicating intense swelling of all four paws and tail, is 19. The animals are then sacrificed; the hind paws of each animal are removed and weighed. The percent inhibition is calculated by comparing the weight increase of the hind paws of the test animals versus the control animals.

EXAMPLE 31

Adjuvant-Induced Arthritis Assay Using
3-(3,5-di-t-butyl-4-hydroxybenzoyl)pyrrole The "AI" assay, as described in Example 29, was performed using 3-(3,5-di-t-butyl-4-hydroxybenzoyl)pyrrole (prepared according to Example 2) as the test material.

A daily dose of 0.4 mg/kg of body weight resulted in a 54% inhibition of hind paw weight increase, and a daily dose of 2.0 mg/kg of body weight resulted in a 70% inhibition of hind paw weight increased, as compared to control animals that did not receive the 3-(3,5-di-t-butyl-4-hydroxybenzoyl)pyrrole.

EXAMPLE 32

Carrageenan-Induced Rat Paw Inflammation Assay "CI"

Anti-inflammatory activity is determined by the Carrageenan-Induced Rat Paw Inflammation "CI" Assay, as is well accepted in the art. A modification of the assay described by Winter, et al., supra., is performed as follows:

Female albino rats (Sim: (SD)fbr) weighing 80–90 g receive the test materials orally in 1 ml aqueous solution at hour 0. One hour later (hr 1) 0.05 ml of a 1% solution (in aqueous 0.9% NaCl) of carrageenan is injected into the right hind paw to inflame the paw. The rats are sacrificed at hour 4, at which time both hind paws are removed and individually weighed. The percent increase in the weight of the inflamed paw over that of the opposite non-inflamed paw is calculated, and the results are reported according to the formula:

$$\frac{\text{wt right paw} - \text{wt left paw}}{\text{wt left paw}} \times 100 = \%\text{increase.}$$

EXAMPLE 33

Arachidonic Acid-Induced Mouse Ear Edema Assay "AAI"

Topical anti-inflammatory activity is determined by the Arachidonic Acid-Induced Mouse Ear Edema "AAI" Assay, as is well accepted in the art. A modification of the assay described by Young, et al., supra., is performed as follows:

The test materials are prepared as solutions in acetone and applied to the right ears of mice, in groups of eight (8), at hour 0. At hour 1, 2 mg of arachidonic acid in acetone solution is applied to the right ears of the mice to induce an inflammatory response. The left ears of these animals serves as negative controls. At hour 2 the mice are sacrificed; their ears are removed and 8 mm diameter full thickness plugs are cut from the tip of each ear. The plugs are weighed and the mean right and left plug weights are calculated for each group. The results are expressed as percent inhibition of ear plug weight increase relative to a positive control group receiving only acetone at hour 0.

EXAMPLE 34

Phenylquinone-Induced Mouse Writhing Assay "PI"

Cyclooxygenase-inhibition activity is determined by the Phenylquinone-Induced Mouse Writhing "PI" Assay, as is well accepted in the art. A modification of the assay described by Hendershot, et al., supra., is performed as follows:

Phenylquinone solution is prepared as follows: 4 mg of phenylquinone is dissolved in 0.5 ml of absolute ethanol, after which 19.5 ml of warmed distilled water is added. When properly prepared, all of the phenylquinone solution remains in solution. The solution is used soon after preparation The test materials are administered in 0.2 ml of an aqueous vehicle at hour 0 to groups of eight male Swiss-Webster (Simonsen) mice weighing about 18–20 g. At either twenty (20) minutes or one hundred twenty (120) minutes later, 0.25 ml of a 0.02% solution of phenylquinone is injected into each animal, to induce writhing. The animals are then observed for the next ten (10) minutes for writhing responses, and the number of writhes per animal is recorded. The mean number of writhes is calculated for each treatment group and the results are expressed as percent inhibition of writhing responses relative to a control group receiving vehicle alone.

EXAMPLE 35

Human Polymorphonuclear Leukocyte Assay "HPMN"

Lipoxygenase inhibition activity is determined in vitro by the Human Polymorphonuclear Leukocyte ("HPMN") Assay, as is well accepted in the art. A modification of the assay described by Radmark, et al., supra., is performed as follows:

1. Preparation of the cells: The HPMNs are prepared from 200–300 ml of heparinized blood of healthy donors not receiving any medication for at least 7 days, using Ficol-Hypaque gradients. In general, HPMNs are greater than 90% pure and their viability is assessed by dye-exclusion to be better than 95%. The cells are suspended in phosphate buffered saline containing 1.0 mM $CaCl_2$ (PH 7.4) and 0.1% ovalbumin, and used within 30 minutes.

2. Lipoxygenase Assay: Incubations are carried out at 37° C. for 5 minutes in a total volume of 0.2 ml arachidonic acid 1-$C^{14}$ ($1 \times 10^{-4}$M unless otherwise indicated, and approximately 300,000 cpm) is added to a suspension of cells (ca $5 \times 10^6$) to initiate the reaction. Prior to the addition of above substrate, the test substances are added to the cells at appropriate concentrations and pre-incubated at 37° C. for 5 minutes. In general, stock solutions of test substances are prepared in ethanol (or other appropriate solvents) and diluted with either incubation-buffer or water. The final concentration of ethanol in the incubation does not exceed 1%. Boiled enzyme blanks and controls containing no test compound are always included. The incubations are terminated by the addition of 0.6 ml of methanol, vortexed and kept on ice for 30 minutes.

1.6 Ml of deionized water is added, vortexed, and centrifuged. The supernatants are decanted and kept in the freezer overnight. Separation of arachidonic acid and lipoxygenase products are carried out using "Baker" disposable $C^{-18}$ extraction columns (1 ml capacity). The columns are prewashed with MeOH (2.0 ml) followed by deionized water (2 ml). After most of the solvent is removed, 2.0 ml of the supernatant is applied to the extraction columns and the solvent is allowed to flow through. The columns are then washed with 5 ml of deionized water and the eluate is discarded. The columns are then eluted with 6.0 ml of a solvent mixture (acetonitrite:$H_2O$:acetic acid in the proportion 50:50:0.1) which recovers all the arachidonic acid metabolites including 5-HETE and $LTB_4$ with very little of arachidonic acid (AA) being eluted (less than 2–3% of incubated counts). The columns are then eluted with 2.0 ml of methanol (forced through by $N_2$) which elutes all of the unreacted substrate AA. The eluates are collected in scintillation vials and 1.0 ml aliquot from each of the two fractions are counted for radioactivity in a Packard liquid scintillation counter. From the radioactivity data thus obtained percent yields of total lipoxygenase products in blanks, controls and drug-containing tubes are calculated as well as percent inhibition by the test compounds.

EXAMPLE 36

Synthesis of 2-(3,5-di-t-butyl-4-hydroxybenzoyl)pyrrole 3,5-Di-t-butyl-4-hydroxybenzoic acid (0.5 g) was suspended in 20 ml of dry methylene chloride and 300 mg of thionyl chloride was added, followed by 7 drops of dry dimethylformamide. All dissolved rapidly at room temperature. After 20 minutes, a sample treated with methanol showed no acid left. The solution was evaporated to dryness, then azeotropically distilled twice with benzene to remove excess thionyl chloride. The residue was dissolved in benzene, 2 ml pyrrole was added and the mixture was refluxed for 30 minutes. 2 Ml more of pyrrole was added and the mixture was refluxed for 1 hour more. After cooling, the mixture was added to a short $SiO_2$ column and eluted with benzene. Elution with $CH_2Cl_2$ gave the product, 0.325 g (54%), homogeneous on tlc.

A repetition of the reaction using the acid chloride derived from 3.0 g of acid, and a total of 24 ml pyrrole in 125 ml benzene for a total reflux time of 2.5 hours gave 1.61 g homogeneous product (mp 145.5°–146.5° C.).

Analysis calculated for $C_{19}H_{25}NO_2$ (m.w. 299.398): Theoretical: C, 76.22; H, 8.42; N, 4.68. Found: C, 76.02; H, 8.16; N, 4.72.

EXAMPLE 37

Comparison of 3-(3,5-di-t-butyl-4-hydroxybenzoyl)pyrrole with 2-(3,5-di-t-butyl-4-hydroxybenzoyl)pyrrole Side by side studies were undertaken to compare the anti-inflammatory activity of 3-(3,5-di-t-butyl-4-hydroxybenzoyl)pyrrole (material "A", a compound of this invention prepared according to Example 2A) with that of 2-(3,5-di-t-butyl-4-hydroxybenzoyl)pyrrole (material "B", a known compound prepared according to Example 36). The assays described in Examples 32–35 were performed using materials "A" and "B", and the results are reported below in Table I.

TABLE I

| | "A" | | "B" | |
|---|---|---|---|---|
| Assay | Dose | Inibition | Dose | Inhibition |
| CI | 1.0 mg/kg | 24% | 100.0 mg/kg | 30% |
| | 10.0 mg/kg | 44% | | |
| AAI | 0.5 mg/ear | 49% | 2.0 mg/ear | 22% |
| | 1.0 mg/ear | 62% | | |
| | 2.0 mg/ear | 67% | | |
| | 2.0 mg/ear | 69% | | |
| PI | | | | |
| (20 min) | 0.1 mg/kg | 15% | 5.0 mg/kg | 26% |
| | 1.0 mg/kg | 61% | 15.0 mg/kg | 40% |
| | 1.5 mg/kg | 100% | 15.0 mg/kg | 52% |
| | 5.0 mg/kg | 99% | 15.0 mg/kg | 65% |
| | 15.0 mg/kg | 97% | 50.0 mg/kg | 56% |
| | 15.0 mg/kg | 96% | 50.0 mg/kg | 38% |
| (120 min) | 15.0 mg/kg | 100% | 15.0 mg/kg | 49% |
| HPMN | 28.0 μg | 50% | 36.0 μg | 50% |

The results shown in Table 1 demonstrate that the anti-inflammatory activity of the present invention (exemplified by material "A") is greatly enhanced over the closest known anit-inflammatory agents (exemplified by material "B").

EXAMPLE 38

Formulations

The following example illustrates the preparation of representative pharmaceutical formulations containing an active compound of Formula X, e.g., 3-(3,5-di-t-butyl-4-hydroxybenzoyl)pyrrole.

38A. I.V. Formulation

| | |
|---|---|
| Active compound | 0.1 g |
| Propylene glycol | 20.0 g |
| Polyethylene glycol 400 | 20.0 g |
| Tween 80 | 1.0 g |
| 0.9% Saline solution qs | 100.0 mL |

The active compound is dissolved in propylene glycol, polyethylene glycol 400 and Tween 80. A sufficient quantity of 0.9% saline solution is then added with stirring to provide 100 mL of the I.V. solution which is filtered through a 0.2 micron membrane filter and packaged under sterile conditions.

38B. Tablet Formulation

| | parts by weight |
|---|---|
| Active compound | 5.0 |
| Magnesium stearate | 0.75 |
| Starch | 0.75 |
| Lactose | 29.0 |
| PVP (polyvinylpyrrolidone) | 0.75 |

The above ingredients are combined and granulated using methanol as the solvent. The formulation is then dried and formed into tablets (containing 2 mg of active compound) with an appropriate tabletting machine.

38C. Formulations With Other Active Ingredients

Other compounds of Formula X, such as those prepared in accordance with Examples 2-29, can be used as the active compound in the preparation of the formulations of this example.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A compound represented by the formula:

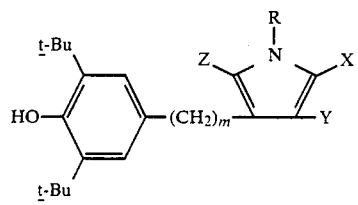

wherein:
m is an integer from one to three;

R is hydrogen, lower alkyl, halo, carboxy lower alkylene, phenyl, benzyl, or a removable directing group; and X, Y and Z are independently selected from hydrogen, lower alkyl, halo, SCN, SR', SOR", SO$_2$R" and CF$_3$;

wherein R' is H, aryl, lower alkyl or lower alkanoyl; and R" is lower alkyl;

or a pharmaceutically acceptable salt thereof.

2. A compound represented by the formula:

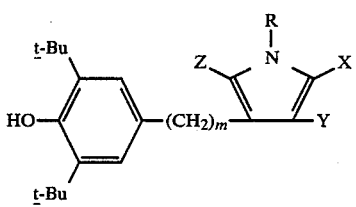

wherein:
m is an integer from one to three;
R is hydrogen, lower alkyl, carboxy lower alkylene, phenyl or benzyl; and
X, Y and Z are independently selected from hydrogen, lower alkyl, halo, SCN, SR', SOR", SO$_2$R" and CF$_3$;
wherein R' is H, aryl, lower alkyl or lower alkanoyl; and R" is lower alkyl;
or a pharmaceutically acceptable salt thereof.

3. The compound of claim 2 wherein: m is one and R is hydrogen.

4. The compound of claim 2 wherein all non-hydrogen X, Y and Z substituents are identical.

5. The compound of claim 2 wherein: lower alkyl is methyl or ethyl; halo is chloro or bromo; and lower alkanoyl is acetyl.

6. The compound of claim 3 wherein: lower alkyl is methyl or ethyl; halo is chloro or bromo; and lower alkanoyl is acetyl.

7. The compound of claim 3 wherein: X, Y and/or Z is hydrogen or chloro.

8. The compound of claim 7 wherein X, Y and Z are chloro.

9. The compound of claim 7 wherein: X is chloro; and Y and Z are hydrogen.

10. The compound of claim 7 wherein: X, Y and Z are hydrogen.

11. The compound of claim 3 wherein: X is thiocyano; and Y and Z are hydrogen.

12. The compound of claim 2 wherein: m is one; R is hydrogen; and X, Y and Z are hydrogen.

13. A pharmaceutical composition comprising a therapeutically effective amount of a compound of claim 2, or a pharmaceutically acceptable salt thereof, in admixture with a pharmaceutically acceptable carrier.

14. A method for the treatment of inflammatory diseases, pain and/or pyrexia in a mammal, said method comprising administering an effective amount of a compound having the structural formula:

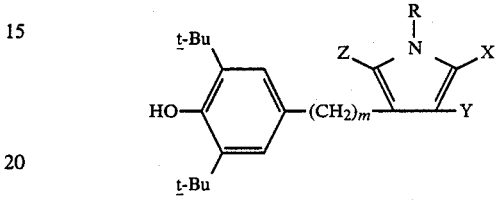

wherein:
m is an integer from one to three;
R is hydrogen, lower alkyl, carboxy lower alkylene, phenyl or benzyl; and
X, Y and Z are independently selected from hydrogen, lower alkyl, halo, SCN, SR', SOR", SO$_2$R" and CF$_3$;
wherein R' is hydrogen, aryl, lower alkyl or lower alkanoyl; and R" is lower alkyl;
or a pharmaceutically acceptable salt thereof.

15. The method of claim 14 wherein the mammal is a human.

16. The method of claim 14 wherein the route of administration is oral.

17. The method of claim 14 wherein: m is one; R is hydrogen; and all non-hydrogen X, Y and Z substituents are identical.

18. The method of claim 17 wherein X, Y and Z are hydrogen.

19. The method of claim 17 wherein X, Y and Z are chloro.

20. The method of claim 17 wherein: X is chloro; and Y and Z are hydrogen.

21. The method of claim 17 wherein: X is thiocyano; and Y and Z are hydrogen.

* * * * *